(12) United States Patent
Manfredsson et al.

(10) Patent No.: US 10,144,932 B2
(45) Date of Patent: Dec. 4, 2018

(54) NURR1 AS A GENETIC TARGET FOR TREATING LEVODOPA-INDUCED DYSKINESIAS IN PARKINSON'S DISEASE

(71) Applicant: Board of Trustees of Michigan State University, East Lansing, MI (US)

(72) Inventors: Fredric P. Manfredsson, Grand Rapids, MI (US); Jack W. Lipton, Grand Rapids, MI (US); Nicholas Kanaan, Grand Rapids, MI (US); Timothy Collier, Grand Rapids, MI (US); Kathy Steece-Collier, Grand Rapids, MI (US); Caryl E. Sortwell, Grand Rapids, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 15/316,726

(22) PCT Filed: Jun. 5, 2015

(86) PCT No.: PCT/US2015/034435
§ 371 (c)(1),
(2) Date: Dec. 6, 2016

(87) PCT Pub. No.: WO2015/188077
PCT Pub. Date: Dec. 10, 2015

(65) Prior Publication Data
US 2017/0198295 A1    Jul. 13, 2017

Related U.S. Application Data

(60) Provisional application No. 62/008,715, filed on Jun. 6, 2014.

(51) Int. Cl.
*A61K 48/00*    (2006.01)
*C12N 15/113*    (2010.01)
*C12N 7/00*    (2006.01)

(52) U.S. Cl.
CPC ............ *C12N 15/1138* (2013.01); *C12N 7/00* (2013.01); *C12N 2310/14* (2013.01); *C12N 2310/141* (2013.01); *C12N 2310/531* (2013.01); *C12N 2320/32* (2013.01); *C12N 2330/51* (2013.01); *C12N 2750/14143* (2013.01)

(58) Field of Classification Search
None
See application file for complete search history.

(56) References Cited

U.S. PATENT DOCUMENTS

| | | |
|---|---|---|
| 7,037,657 B2 | 5/2006 | Le et al. |
| 2006/0040298 A1 | 2/2006 | Schmidt et al. |
| 2011/0105593 A1 | 5/2011 | Steel et al. |
| 2011/0268748 A1* | 11/2011 | Federoff ............ C07K 14/4705 424/172.1 |
| 2012/0083002 A1 | 4/2012 | Baik et al. |
| 2012/0213860 A1 | 8/2012 | Bessiere |
| 2017/0209441 A1* | 7/2017 | Rawat .................. A61K 31/506 |

OTHER PUBLICATIONS

DiFiglia et al. (PNAS 2007, vol. 104: 17204-17209).*
Han et al. (J. Nat. Prod. 2016, 79, 1604-1609).*

* cited by examiner

*Primary Examiner* — Kimberly Chong
(74) *Attorney, Agent, or Firm* — Foley Hoag LLP; DeAnn F. Smith

(57) ABSTRACT

Methods of treating movement disorders by reducing the activity of Nurr1 are disclosed. These methods are particularly applicable to subjects suffering from Parkinson's disease who have either developed levodopa-induced dyskinesia (LID) or are at risk of developing LID. In some aspects, the invention relates to a method for treating a movement disorder in a subject in need thereof, comprising administering to the subject a therapeutically effective amount of a composition, wherein said composition reduces the activity of a nuclea receptor related 1 protein ("Nurr1"). In some embodiments, the movement disorder is a dyskinesia. The movement disorder may be a levodopa-induced dyskinesia.

16 Claims, 1 Drawing Sheet
Specification includes a Sequence Listing.

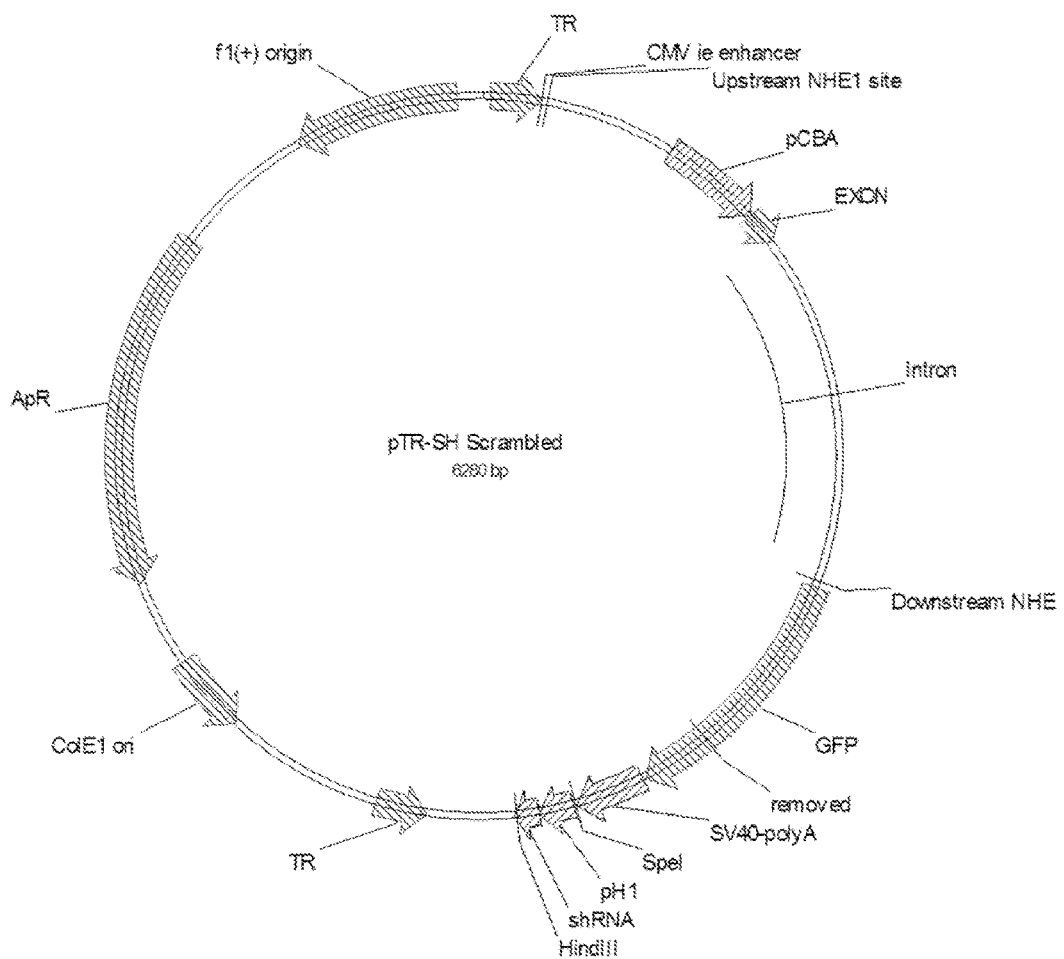

SEQUENCE LISTING

<160> NUMBER OF SEQ ID NOS: 14

<210> SEQ ID NO 1
<211> LENGTH: 3546
<212> TYPE: DNA
<213> ORGANISM: Homo sapiens

<400> SEQUENCE: 1

```
gctgacgcgc gctgacgcgc ggagacttta ggtgcatgtt ggcagcggca gcgcaagcca      60
cataaacaaa ggcacattgg cggccagggc cagtccgccc ggcggctcgc gcacggctcc     120
gcggtcccct tgcctgtcc agccggccgc ctgtccctgc tccctccctc cgtgaggtgt     180
ccgggttccc ttcgcccagc tctcccaccc ctacccgacc ccggcgcccg ggctcccaga     240
gggaactgca cttcggcaga gttgaatgaa tgaagagaga cgcggagaac tcctaaggag     300
gagattggac aggctggact ccccattgct tttctaaaaa tcttggaaac tttgtccttc     360
attgaattac gacactgtcc acctttaatt tcctcgaaaa cgcctgtaac tcggctgaag     420
ccatgccttg tgttcaggcg cagtatgggt cctcgcctca aggagccagc cccgcttctc     480
agagctacag ttaccactct tcgggagaat acagctccga tttcttaact ccagagtttg     540
tcaagtttag catggacctc accaacactg aaatcactgc caccacttct ctccccagct     600
tcagtacctt tatggacaac tacagcacag gctacgacgt caagccacct tgcttgtacc     660 aaatgccccct gtccggacag cagtcctcca ttaaggtaga agacattcag atgcacaact     720
accagcaaca cagccacctg cccccccagt ctgaggagat gatgccgcac tccgggtcgg     780
tttactacaa gccctcctcg ccccgacgc ccaccacccc gggcttccag gtgcagcaca     840
gccccatgtg ggacgacccg ggatctctcc acaacttcca ccagaactac gtggccacta     900
cgcacatgat cgagcagagg aaaacgccag tctcccgcct ctcctcttc tcctttaagc     960 aatcgccccc tggcacccg gtgtctagtt gccagatgcg cttcgacggg ccctgcacg    1020 tccccatgaa cccggagccc gccggcagcc accacgtggt ggacgggcag accttcgctg    1080
tgcccaaccc cattcgcaag ccccgcgtcca tgggcttcca gggcctgcag atcggccacg    1140
cgtctcagct gctcgacacg caggtgccct caccgccgtc gcgggggctcc cctccaacg    1200 agggggctgtg cgctgtgtgt ggggacaacg cggcctgcca acactacggc gtgcgcacct    1260
```

```
gtgagggctg caaaggcttc tttaagcgca cagtgcaaaa aaatgcaaaa tacgtgtgtt      1320
tagcaaataa aaactgccca gtggacaagc gtcgccggaa tcgctgtcag tactgccgat      1380
ttcagaagtg cctggctgtt gggatggtca agaagtggt tcgcacagac agtttaaaag      1440
gccggagagg tcgtttgccc tcgaaaccga agagcccaca ggagccctct cccccttcgc      1500
ccccggtgag tctgatcagt gccctcgtca gggcccatgt cgactccaac ccggctatga      1560
ccagcctgga ctattccagg ttccaggcga accctgacta tcaaatgagt ggagatgaca      1620
cccagcatat ccagcaattc tatgatctcc tgactggctc catggagatc atccggggct      1680
gggcagagaa gatccctggc ttcgcagacc tgcccaaagc cgaccaagac ctgctttttg      1740
aatcagcttt cttagaactg tttgtccttc gattagcata caggtccaac ccagtggagg      1800
gtaaactcat ctttttgcaat ggggtggtct tgcacaggtt gcaatgcgtt cgtggctttg      1860
gggaatggat tgattccatt gttgaattct cctccaactt gcagaatatg aacatcgaca      1920
tttctgcctt ctcctgcatt gctgccctgg ctatggtcac agagagacac gggctcaagg      1980
aacccaagag agtggaagaa ctgcaaaaca agattgtaaa ttgtctcaaa gaccacgtga      2040 cttcaacaa tggggggttg aaccgcccca attatttgtc caaactgttg gggaagctcc      2100
cagaacttcg tacccttgc acacagggc tacagcgcat tttctacctg aaattggaag      2160
acttggtgcc accgccagca ataattgaca aactttttcct ggacactta cctttctaag      2220 acctcctccc aagcacttca aggaactgg aatgataatg gaaactgtca agaggggca      2280 agtcacatgg gcagagatag ccgtgtgagc agtctcagct caagctgccc cccatttctg      2340
taaccctcct agccccttg atccctaaag aaaacaaaca aacaaacaaa aactgttgct      2400
atttcctaac ctgcaggcag aacctgaaag ggcattttgg ctccggggca tcctggattt      2460
agaacatgga ctacacacaa tacagtggta taaacttttt attctcagtt taaaaatcag      2520
tttgttgttc agaagaaaga ttgctataat gtataatggg aaatgtttgg ccatgcttgg      2580
ttgttgcagt tcagacaaat gtaacacaca cacacataca cacacacaca cacacagaa      2640 gacacatctt aaggggaccc acaagtattg cccttaaca agacttcaaa gttttctgct      2700
gtaaagaaag ctgtaatata tagtaaaact aaatgttgcg tgggtggcat gagttgaaga      2760
aggcaaaggc ttgtaaattt acccaatgca gtttggcttt ttaaattatt ttgtgcctat      2820
ttatgaataa atattacaaa ttctaaaaga taagtgtgtt tgcaaaaaaa aagaaaataa      2880
atacataaaa aagggacaag catgttgatt ctaggttgaa aatgttatag gcacttgcta      2940
cttcagtaat gtctatatta tataaatagt atttcagaca ctatgtagtc tgttagattt      3000
tataaagatt ggtagttatc tgagcttaaa catttctca attgtaaaat aggtgggcac      3060
aagtattaca catcagaaaa tcctgacaaa agggacacat agtgttgta acaccgtcca      3120 acattccttg tttgtaagtg ttgtatgtac cgttgatgtt gataaaaaga agtttatat      3180 cttgattatt ttgttgtcta aagctaaaca aaacttgcat gcagcagctt ttgactgttt      3240
ccagagtgct tataatatac ataactccct ggaaataact gagcactttg aattttttt      3300 atgtctaaaa ttgtcagtta attttattatt ttgtttgagt aagaattta atattgccat      3360 attctgtagt attttttcttt gtatatttct agtatggcac atgatatgag tcactgcctt      3420
tttttctatg gtgtatgaca gttagagatg ctgattttt ttctgataaa ttctttctttt      3480 gagaaagaca attttaatgt ttacaacaat aaaccatgta aatgaacaga aaaaaaaaa      3540 aaaaaa                                                                3546
```

<210> SEQ ID NO 2
<211> LENGTH: 8344
<212> TYPE: DNA
<213> ORGANISM: Homo sapiens

<400> SEQUENCE: 2

```
gctgacgcgc gctgacgcgc ggagacttta ggtgcatgtt ggcagcggca gcgcaagcca      60
cataaacaaa ggcacattgg cggccagggc cagtccgccc ggcggctcgc gcacggctcc     120
gcggtccctt ttgcctgtcc agccggccgc ctgtccctgc tccctccctc cgtgaggtgt     180
ccgggttccc ttcgcccagc tctcccaccc ctacccgacc ccggcgcccg ggctcccaga     240
gggaactgca cttcggcaga gttgaatgaa tgaagacaga cgcggagaac tcctaagtga     300
gtagatgcag cccatgcagt tcgccttctt ttatgctttt tccttctttt gcacgtctct     360
tcttttccact tgtgtgggac aggttctctg gaagtgggag ccagaggctt ctagtgagag     420
tgggaccgaa ggatggggag tgcgtgcgcg cagttaccgg ggggcatttg ttcgaactcc     480
ggctttggca ctagtgggga gttggctctc gacagaggtt tccaggctcc tcattggtgg     540
acgtggaagg gagactccac agtttgggag ctgaggacta gcccgcggaa atgtgcgcaa     600
agtttgctgt tagtgaggaa ttgattgtgg cctgtgaaca cggagactcc aagtcctatg     660
tatacgaggg aagctgccca caaactgaca gggagaggaa gttcttcagt ttatgcgttg     720
cttgggaact gtgtctccgc ggctggccag cgcgcgatgt ttcccgggta ttgttgagta     780
agggtggtgt tggtagcgtg tcctgttact aagttgcctg aaatttctgg ttttgacata     840
tgctgtcctt gggtttgcga atgtatcaga gcgagaatat gaatatgtaa agagtacagt     900
tatgaaactg tggagctacc aggggggttaa tatccaacac aggaatatct ctaagggctg     960
tggggttcga gtctcctttc tgcttttttct gggtaatctt ccccccaccc ccaccaccac    1020
tatgaagcaa gattgtgggg gaggggaaag aataaaaaga gaggatactg ctttcttttt    1080
ttcattagta ataagattgt ctgtgctcta gaatgtcttc caagtgggaa catctgaaaa    1140
ttgctaggac acaagaatgc cttgttccag aaaggcagat tgtggaaggc attatgggga    1200
aggtgttcat cttgctgtgc tgggaaacac ttctaatatt ggtgccaata ccatataagc    1260
agtatgtccc ccctctgcaa ttgacctaag aagctcctgg aaaagtagat cccctcttcc    1320
caccttgtga ccattaagcc ttgtgaccat taaagatgct gaaagacaag ttttctggaa    1380
aagtgaacat caatttatct gtagctccaa tcccagtgct ctgtcaaaag cactttagaa    1440
gtgcggatgc ttccactcaa cttgccttct cagtcaaggc cttctaaca ttttgtaagg    1500
gggaagattg ttttctcatt ttatattctt gacttctact ttcttcccct ctaccaaaag    1560
aaaaggcaat ttcaccacaa gaaaaaaaaa tgcaagagaa ggttccaatg ctgtatttc    1620
atactctagt cttcatactc aggtcctgaa ttaacctaag atggaaatga cctctccacc    1680
tacactgtag caaaggggcc agttcattac atcataaatg ttaaatgagt tcatggacta    1740
gctttcctct tgcaggatct tctctctgca aggatttaca cagtgcaatg ggtggtattt    1800
tctgttgttt caagtcattt cttttataca ttcattttaa gtgctatgtt tggtaaaggc    1860
ttcccactca tttccaatga gacaaacagg gaaggcatgg aagggcctgc ctggtgagtc    1920
tacatatgcc cagctgaatc tctgtcggga agaaaccctg aagcttcctg tgtctgtatt    1980
tcagggagga gattggacag gctggactcc ccattgcttt tctaaaaatc ttggaaactt    2040
tgtccttcat tgaattacga cactgtccac ctttaatttc ctcgaaaacg cctgtaactc    2100
ggctgaaggt tagtgcaact tcatttcttt cctttactct ccagagctcc ccaaacatca    2160
```

```
agaaacagga caaggcaaac cctgtaactt aaggtttgcc cgacccatcg ccttcgggaa    2220
caactttctc attgtgaaat tcaacttcat ttctagatgg tcatttctag aaagagactg    2280
ctgaatctga gcttcagaga agaggctcat ctgagtggga tgagtggggg ggtatgaggg    2340
agatgtttgg aaatacccag gagtgtagac cctcagtagc ttttagctc tgggtcttta    2400 tttggttagt ctttccacgc cctaaactgt tgttctgcag cattctctct ctcctgcctt    2460
tcctctcgcg cccctacatg ctctctgact gccgcgggct gccggtgtag ctccaggtgt    2520
acccgagccc gggagaaagt gttcagttga ccaggctgag tgtgttatca ccctgtttca    2580
tttccagcca tgccttgtgt tcaggcgcag tatgggtcct cgcctcaagg agccagcccc    2640
gcttctcaga gctacagtta ccactcttcg ggagaataca gctccgattt cttaactcca    2700
gagtttgtca agtttagcat ggacctcacc aacactgaaa tcactgccac cacttctctc    2760
cccagcttca gtacctttat ggacaactac agcacaggct acgacgtcaa gccaccttgc    2820
ttgtaccaaa tgcccctgtc cggacagcag tcctccatta aggtagaaga cattcagatg    2880
cacaactacc agcaacacag ccacctgccc ccccagtctg aggagatgat gccgcactcc    2940
gggtcggttt actacaagcc ctcctcgccc ccgacgccca ccaccccggg cttccaggtg    3000
cagcacagcc ccatgtggga cgacccggga tctctccaca acttccacca gaactacgtg    3060
gccactacgc acatgatcga gcagaggaaa acgccagtct cccgcctctc cctcttctcc    3120
tttaagcaat cgcccctgg cacccggtg tctagttgcc agatgcgctt cgacgggccc    3180
ctgcacgtcc ccatgaaccc ggagcccgcc ggcagccacc acgtggtgga cgggcagacc    3240
ttcgctgtgc ccaaccccat tcgcaagccc gcgtccatgg gcttcccggg cctgcagatc    3300
ggccacgcgt ctcagctgct cgacacgcag gtgccctcac cgccgtcgcg gggctccccc    3360
tccaacgagg ggctgtgcgc tgtgtgtggg acaacgcgg cctgccaaca ctacggcgtg    3420
cgcacctgtg agggctgcaa aggcttcttt aaggtgagca atggcgggag cggagtaggc    3480
aggtagggag cccctagtgc ccgggacctc ggagtgtgcc ctctgccttg gtgccagtag    3540
cccagcccca gctctcccgg gactgcccag ctctccgggg tccgccgaag ctgccctgca    3600
ggagaccatg ggctgcggcg gggacttccg ggtgtctgag aaagggaagc agaaagactg    3660
ggaggccagg gtcgcatccc cctcgcattc agccgacccg gctggccccc gcccgaagtt    3720
gctggagccg gagttggaag agggtcattt gcatgtgcta ggagctgtct tccctgttca    3780
gaatgaaatt ggttaggaca gagaaccgtg tctgagctaa ccaagtggaa cagaattccc    3840
tatggtcaaa ttaagtgatc tcttatttc gccatcctga ttgaataatc ttatcatttt    3900
aaatagagaa ggtctccaag gaatgtaaat aatatgaatg cccacggatt tgtatttact    3960
gagcgtctcc ttctccttct cttggcatat aaaacacagc aaggagcggc aaggttagct    4020
caaatgttaa cgctatcaat tttcttctgt taaatgccct gggggaggaa aaagaaaag    4080 aaagaagaa aaggaagaga aaaaaataaa atggaattgt gtgtatgtgt ttgtttgtgg    4140
ggaggaatcg tagaccccag tcacataaca gaaattttct ccgagttgcc tgattttcaa    4200
aagaagaaaa aaaatgttgg tctatattgt ctccttttgc agcgcacagt gcaaaaaaat    4260
gcaaaatacg tgtgtttagc aaataaaaac tgcccagtgg acaagcgtcg ccggaatcgc    4320
tgtcagtact gccgatttca gaagtgcctg gctgttggga tggtcaaaga aggtaggctg    4380
aggggagctg ccgacccctcc agtttgcgcc tttaggaaac cactgctcat actccagcat    4440
cacgttccac ttcccggtgc tggggatctc cgactccccc tcagtatggc ctccaggacc    4500
```

```
ctgcagctgc ctgcttgccc ggccttccct agagaaagcc gccaggccct tctctccttt    4560
aactatacga cccatttgga ggaagacata aaataacccc gcattttta atgcttctag     4620 tcagtgaagg ctttacaagc actggggccc tcagccgctc agcctggtgc cccgcggctg    4680
cggccttccc cggggaggga ccgaggcagc agctgggcct gggctcggaa aagcggcgct    4740
aacagggctc ttcctttgca gtggttcgca cagacagttt aaaaggccgg agaggtcgtt    4800
tgccctcgaa accgaagagc ccacaggagc cctctccccc ttcgcccccg gtgagtctga    4860
tcagtgccct cgtcagggcc catgtcgact ccaacccggc tatgaccagc ctggactatt    4920
ccagggtaag aagctggcgg gggggatatc atgtggacaa accgacagat gggcaggacc    4980
cctccccaca tccgtcatta actctcagat tcaacggggg taaagaaggc aagcaaggct    5040
gtatatgcct cgcagctctg gccagggcct caagattcag atcttcagac aatccatgta    5100
gctgggggca tagacatgag gacaggatgg aggaaggagg agagggacac gccacagggt    5160
ttgaagctgt gtgaattccc actacccac tacccatcg cccctcctct tccatataca      5220
ccagtgcctc taccatgaaa tccaggggct gtgcaaactc tcccccttcc caatctactt    5280
tattcccagt cctccataga gatagatgct ttaatcctca tccttcctgg cactgtgctg    5340
gggaaggatg tgggggcctg tctggggtc agggaaggga aggagagggt gtaaagaatg     5400
ccagtggggt gggggatcaa gtggtcagat ccttttact ccagctgtga aaaatatgcg     5460
ggctttaatt ggaggaagta tgttgagcaa acctggtagg gactgcaatt ttattaagat    5520
ttgcaaaagg gcgtctcagc tcgaggccca ctctgggact agcatgaata ctaacatgtc    5580
aattgttttg tggagataag agtgaacgtt cccagggct ggatggcact gtatttagtc     5640
tgtatggaaa tggcaattta catatttaaa gcagcgacct cgtagcacca tccctaattg    5700
aattaattgc cccggaacat ctaatttcct tactggtcag agagggttt aattgttata     5760 aaaacctggc tcccctatta gaaacggggt tagcaatttc acgggttata tattttagag    5820
aacctcatta agtgcttttt aaaatgaaat tccagttcca ggcgaaccct gactatcaaa    5880
tgagtggaga tgacacccag catatccagc aattctatga tctcctgact ggctccatgg    5940
agatcatccg gggctgggca gagaagatcc ctggcttcgc agacctgccc aaagccgacc    6000
aagacctgct tttgaatca gctttcttag aactgtttgt ccttcgatta gcatacaggt      6060
aataagggag ggagggagac aatccaggga ggctgtgaga gaaatcaaga aaggaaagga    6120
aagggaggaa gggaaaccag agggtggggt agagaaaaag acagaatagg aaatggaagt    6180
cggagaaagg aagaaaaaga aagaaaacaa aaaaagacga gaagaagcga gcccagaagc    6240
cttggatgaa tggaatggag gtgggatagg gggcgttctt gattgttatg aaattaaacc    6300 cttttcaaggt ccactggtct acatttttatt aactcttcag taattaggtg actcttaaat  6360
ccctcattta ttgctcttca agtaattagt tgtttagctt ttctctctct cttttctcc     6420 cctctctctc tttggtatta attgcaggtc caacccagtg gagggtaaac tcatcttttg    6480
caatggggtg gtcttgcaca ggttgcaatg cgttcgtggc tttggggaat ggattgattc    6540
cattgttgaa ttctcctcca acttgcagaa tatgaacatc gacatttctg ccttctcctg    6600
cattgctgcc ctggctatgg tcacaggtca gtactgcagg cgcagggcgc ttcccctcca    6660
gaactgccta gcaggatttg tcctgagttt cccttgtcac agattctcct tggttttgcc    6720
aactagctaa ctgtcttgta cattcttctt ttgtttctga ttatgttttc tgcagagaga    6780
cacgggctca aggaacccaa gagagtgaa gaactgcaaa acaagattgt aaattgtctc     6840
aaagaccacg tgactttcaa caatgggggg ttgaaccgcc ccaattattt gtccaaactg    6900
```

-continued

```
ttggggaagc tcccagaact tcgtaccctt tgcacacagg ggctacagcg cattttctac    6960
ctgaaattgg aagacttggt gccaccgcca gcaataattg acaaactttt cctggacact    7020
ttacctttct aagacctcct cccaagcact tcaaggaac tggaatgata atggaaactg     7080
tcaagagggg gcaagtcaca tgggcagaga tagccgtgtg agcagtctca gctcaagctg    7140
ccccccattt ctgtaaccct cctagccccc ttgatcccta agaaaacaa acaaacaaac     7200 aaaaactgtt gctatttcct aacctgcagg cagaacctga aagggcattt tggctccggg    7260
gcatcctgga tttagaacat ggactacaca caatacagtg gtataaactt tttattctca    7320
gtttaaaaat cagtttgttg ttcagaagaa agattgctat aatgtataat gggaaatgtt    7380
tggccatgct tggttgttgc agttcagaca aatgtaacac acacacacat acacacacac    7440
acacacacac agagacacat cttaagggga cccacaagta ttgcccttta acaagacttc    7500
aaagttttct gctgtaaaga aagctgtaat atatagtaaa actaaatgtt gcgtgggtgg    7560
catgagttga agaaggcaaa ggcttgtaaa tttacccaat gcagtttggc ttttttaaatt   7620 attttgtgcc tatttatgaa taaatattac aaattctaaa agataagtgt gtttgcaaaa    7680
aaaaagaaaa taaatacata aaaaagggac aagcatgttg attctaggtt gaaaatgtta    7740
taggcacttg ctacttcagt aatgtctata ttatataaat agtatttcag acactatgta    7800
gtctgttaga ttttataaag attggtagtt atctgagctt aaacattttc tcaattgtaa    7860
aataggtggg cacaagtatt acacatcaga aaatcctgac aaaagggaca catagtgttt    7920
gtaacaccgt ccaacattcc ttgtttgtaa gtgttgtatg taccgttgat gttgataaaa    7980
agaaagttta tatcttgatt attttgttgt ctaaagctaa acaaaacttg catgcagcag    8040
cttttgactg tttccagagt gcttataata tacataactc cctggaaata actgagcact    8100 ttgaatttt tttatgtcta aaattgtcag ttaatttatt attttgtttg agtaagaatt      8160
ttaatattgc catattctgt agtatttttc tttgtatatt tctagtatgg cacatgatat    8220
gagtcactgc cttttttct atggtgtatg acagttagag atgctgattt ttttctgat      8280 aaattctttc tttgagaaag acaattttaa tgtttacaac aataaaccat gtaaatgaac    8340
agaa                                                                  8344
```

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 3
tacagctccg atttcttaa                                                    19

<210> SEQ ID NO 4
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 4
gtacagctcc gatttcttaa ttcaagagat taagaaatcg gagctgtatt tttt            54

<210> SEQ ID NO 5

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cgcgaaatat gtgtgttta                                               19

<210> SEQ ID NO 6
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gcgcgaaata tgtgtgttta ttcaagagat aaacacacat atttcgcgtt tttt        54

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gaccatgtga ctttcaata                                               19

<210> SEQ ID NO 8
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gaccatgtga ctttcaatat tcaagagata ttgaaagtca catggtcttt ttt         53

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gacctcacca acactgaaa                                               19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cagcaataat tgacaaact                                               19

<210> SEQ ID NO 11
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtcctccatt aaggtagaa                                                   19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gggaatggat tgattccat                                                   19

<210> SEQ ID NO 13
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gggaatggat tgattccatt tcaagagaat ggaatcaatc cattcccttt ttt             53

<210> SEQ ID NO 14
<211> LENGTH: 6280
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
gggggggggg ggggggggtt ggccactccc tctctgcgcg ctcgctcgct cactgaggcc      60
gggcgaccaa aggtcgcccg acgcccgggc tttgcccggg cggcctcagt gagcgagcga     120
gcgcgcagag agggagtggc caactccatc actaggggtt cctagatctg aattcggtgc     180
tagcacccta gttattaata gtaatcaatt acggggtcat tagttcatag cccatatatg     240
gagttccgcg ttacataact tacggtaaat ggcccgcctg gctgaccgcc caacgacccc     300
cgcccattga cgtcaataat gacgtatgtt cccatagtaa cgccaatagg gactttccat     360
tgacgtcaat gggtggacta tttacggtaa actgcccact ggcagtaca tcaagtgtat      420 catatgccaa gtacgccccc tattgacgtc aatgacggta aatggcccgc ctggcattat     480
gcccagtaca tgaccttatg gactttcct acttggcagt acatctacgt attagtcatc      540
gctattacca tggtcgaggt gagccccacg ttctgcttca ctctccccat ctccccccc      600 tccccacccc caatttttgta tttatttatt ttttaattat tttgtgcagc gatggggggcg    660 gggggggggg ggggcgcgc gccaggcggg gcggggcggg gcgaggggcg gggcgggcg       720 aggcggagag gtgcggcggc agccaatcag agcggcgcgc tccgaaagtt tccttttatg     780
gcgaggcggc ggcggcggcg ccctataaa aagcgaagcg cgcggcgggc gggagtcgct      840
gcgacgctgc cttcgccccg tgccccgctc cgccgccgcc tcgcgccgcc cgccccggct     900
ctgactgacc gcgttactcc cacaggtgag cgggcgggac ggcccttctc ctccgggctg    960
```

-continued

```
taattagcgc ttggtttaat gacggcttgt ttcttttctg tggctgcgtg aaagccttga    1020
ggggctccgg gagggccctt tgtgcggggg ggagcggctc ggggggtgcg tgcgtgtgtg    1080
tgtgcgtggg gagcgccgcg tgcggcccgc gctgcccggc ggctgtgagc gctgcgggcg    1140
cggcgcgggg ctttgtgcgc tccgcagtgt gcgcgagggg agcgcggccg ggggcggtgc    1200
cccgcggtgc gggggggggct gcgaggggaa caaaggctgc gtgcgggtg tgtgcgtggg    1260
ggggtgagca gggggtgtgg gcgcggcggt cgggctgtaa cccccccctg cacccccctc    1320
cccgagttgc tgagcacggc ccggcttcgg gtgcggggct ccgtacgggg cgtggcgcgg    1380
ggctcgccgt gccgggcggg gggtggcggc aggtgggggt gccgggcggg gcggggccgc    1440
ctcgggccgg ggagggctcg gggagggggc gcggcggccc ccggagcgcc ggcggctgtc    1500
gaggcgcggc gagccgcagc cattgccttt tatggtaatc gtgcgagagg gcgcagggac    1560
ttcctttgtc ccaaatctgt gcggagccga atctgggag gcgccgccgc accccctcta    1620
gcgggcgcgg ggcgaagcgg tgcggcgccg gcaggaagga aatgggcggg gagggccttc    1680
gtgcgtcgcc gcgccgccgt ccccttctcc ctctccagcc tcgggctgt ccgcgggggg    1740
acggctgcct tcggggggga cggggcaggg cggggttcgg cttctggcgt gtgaccggcg    1800
gctctagagc ctctgctaac catgttcatg ccttcttctt tttcctacag ctcctgggca    1860
acgtgctggt tattgtgctg tctcatcatt ttggcaaagt attcctcgaa gatctgctag    1920
caggcgcgcg gccgccgcca ccatgagcaa gggcgaggaa ctgttcactg gcgtggtccc    1980
aattctcgtg gaactggatg gcgatgtgaa tgggcacaaa ttttctgtca gcggagaggg    2040
tgaaggtgat gccacatacg gaaagctcac cctgaaattc atctgcacca ctggaaagct    2100
ccctgtgcca tggccaacac tggtcactac cctgacctat ggcgtgcagt gcttttccag    2160
atacccagac catatgaagc agcatgactt tttcaagagc gccatgcccg agggctatgt    2220
gcaggagaga accatctttt tcaaagatga cgggaactac aagacccgcg ctgaagtcaa    2280
gttcgaaggt gacaccctgg tgaatagaat cgagctgaag gcattgact ttaaggagga    2340
tggaaacatt ctcggccaca agctggaata caactataac tcccacaatg tgtacatcat    2400
ggccgacaag caaaagaatg gcatcaaggt caacttcaag atcagacaca acattgagga    2460
tggatccgtg cagctggccg accattatca acagaacact ccaatcggcg acggccctgt    2520
gctcctccca gacaaccatt acctgtccac ccagtctgcc ctgtctaaag atcccaacga    2580
aaagagagac cacatggtcc tgctggagtt tgtgaccgct gctgggatca cacatggcat    2640
ggacgagctg tacaagtgag cggccgcggg gttccagaca tgataagata cattgatgag    2700
tttggacaaa ccacaactag aatgcagtga aaaaaatgct ttatttgtga aatttgtgat    2760
gctattgctt tatttgtaac cattataagc tgcaataaac aagttaacaa caacaattgc    2820
attcatttta tgtttcaggt tcaggggggag gtgtgggagg ttttttacta gtaattcata    2880
tttgcatgtc gctatgtgtt ctgggaaatc accataaacg tgaaatgtct ttggatttgg    2940
gaatcttata agttctgtat gagaccactc ggatccacaa gatgaagagc accaactcga    3000
gttggtgctc ttcatcttgt tgttttttgg aaaagcttgt cgactagagc tcgctgatca    3060
gcctcgactg tgccttctag ttgccagcca tctgttgttt gcccctcccc cgtgccttcc    3120
ttgaccctgg aaggtgccac tcccactgtc ctttcctaat aaaatgagga aattgcatcg    3180
cattgtctga gtaggtgtca ttctattctg ggggtgggg tgggcagga cagcaagggg    3240
gaggattggg aagacaatag caggcatgct ggggagagat ctaggaaccc ctagtgatgg    3300
agttggccac tccctctctg cgcgctcgct cgctcactga ggccgcccgg gcaaagcccg    3360
```

```
ggcgtcgggc gacctttggt cgcccggcct cagtgagcga gcgagcgcgc agagagggag   3420
tggccaaccc cccccccccc cccctgcag  ccctgcatta atgaatcggc caacgcgcgg   3480
ggagaggcgg tttgcgtatt gggcgctctt ccgcttcctc gctcactgac tcgctgcgct   3540
cggtcgttcg gctgcggcga gcggtatcag ctcactcaaa ggcggtaata cggttatcca   3600
cagaatcagg ggataacgca ggaaagaaca tgtgagcaaa aggccagcaa aaggccagga   3660
accgtaaaaa ggccgcgttg ctggcgtttt tccataggct ccgcccccct gacgagcatc   3720
acaaaaatcg acgctcaagt cagaggtggc gaaacccgac aggactataa agataccagg   3780
cgtttccccc tggaagctcc ctcgtgcgct ctcctgttcc gaccctgccg cttaccggat   3840
acctgtccgc ctttctccct tcgggaagcg tggcgctttc tcaatgctca cgctgtaggt   3900
atctcagttc ggtgtaggtc gttcgctcca agctgggctg tgtgcacgaa ccccccgttc   3960
agcccgaccg ctgcgcctta tccggtaact atcgtcttga gtccaacccg gtaagacacg   4020
acttatcgcc actggcagca gccactggta acaggattag cagagcgagg tatgtaggcg   4080
gtgctacaga gttcttgaag tggtggccta actacggcta cactagaagg acagtatttg   4140
gtatctgcgc tctgctgaag ccagttacct tcggaaaaag agttggtagc tcttgatccg   4200
gcaaacaaac caccgctggt agcggtggtt tttttgtttg caagcagcag attacgcgca   4260
gaaaaaaagg atctcaagaa gatcctttga tcttttctac ggggtctgac gctcagtgga   4320
acgaaaactc acgttaaggg attttggtca tgagattatc aaaaaggatc ttcacctaga   4380
tccttttaaa ttaaaaatga agttttaaat caatctaaag tatatatgag taaacttggt   4440
ctgacagtta ccaatgctta atcagtgagg cacctatctc agcgatctgt ctatttcgtt   4500
catccatagt tgcctgactc cccgtcgtgt agataactac gatacgggag ggcttaccat   4560
ctggccccag tgctgcaatg ataccgcgag acccacgctc accggctcca gatttatcag   4620
caataaacca gccagccgga agggccgagc gcagaagtgg tcctgcaact ttatccgcct   4680
ccatccagtc tattaattgt tgccgggaag ctagagtaag tagttcgcca gttaatagtt   4740
tgcgcaacgt tgttgccatt gctacaggca tcgtggtgtc acgctcgtcg tttggtatgg   4800
cttcattcag ctccggttcc caacgatcaa ggcgagttac atgatccccc atgttgtgca   4860
aaaaagcggt tagctccttc ggtcctccga tcgttgtcag aagtaagttg gccgcagtgt   4920
tatcactcat ggttatggca gcactgcata attctcttac tgtcatgcca tccgtaagat   4980
gcttttctgt gactggtgag tactcaacca agtcattctg agaatagtgt atgcggcgac   5040
cgagttgctc ttgcccggcg tcaatacggg ataataccgc gccacatagc agaactttaa   5100
aagtgctcat cattggaaaa cgttcttcgg ggcgaaaact ctcaaggatc ttaccgctgt   5160
tgagatccag ttcgatgtaa cccactcgtg cacccaactg atcttcagca tcttttactt   5220
tcaccagcgt ttctgggtga gcaaaaacag gaaggcaaaa tgccgcaaaa aagggaataa   5280
gggcgacacg gaaatgttga atactcatac tcttcctttt tcaatattat tgaagcattt   5340
atcagggtta ttgtctcatg agcggataca tatttgaatg tatttagaaa aataaacaaa   5400
taggggttcc gcgcacattt ccccgaaaag tgccacctga cgtctaagaa accattatta   5460
tcatgacatt aacctataaa aataggcgta tcacgaggcc ctttcgtctc gcgcgtttcg   5520
gtgatgacgg tgaaaacctc tgacacatgc agctcccgga gacggtcaca gcttgtctgt   5580
aagcggatgc cgggagcaga caagcccgtc agggcgcgtc agcgggtgtt ggcgggtgtc   5640
ggggctggct taactatgcg gcatcagagc agattgtact gagagtgcac catatgcggt   5700
```

```
gtgaaatacc gcacagatgc gtaaggagaa aataccgcat caggaaattg taaacgttaa    5760
tattttgtta aaattcgcgt taaatttttg ttaaatcagc tcattttta accaataggc     5820 cgaaatcggc aaaatccctt ataaatcaaa agaatagacc gagatagggt tgagtgttgt    5880
tccagtttgg aacaagagtc cactattaaa gaacgtggac tccaacgtca aagggcgaaa    5940
aaccgtctat cagggcgatg gcccactacg tgaaccatca ccctaatcaa gttttttggg    6000
gtcgaggtgc cgtaaagcac taaatcggaa ccctaaaggg agcccccgat ttagagcttg    6060
acggggaaag ccggcgaacg tggcgagaaa ggaagggaag aaagcgaaag gagcgggcgc    6120
tagggcgctg gcaagtgtag cggtcacgct gcgcgtaacc accacaccg ccgcgcttaa     6180 tgcgccgcta cagggcgcgt cgcgccattc gccattcagg ctacgcaact gttgggaagg    6240
gcgatcggtg cgggcctctt cgctattacg ccaggctgca                          6280
```

NURR1 AS A GENETIC TARGET FOR TREATING LEVODOPA-INDUCED DYSKINESIAS IN PARKINSON'S DISEASE

PRIORITY CLAIM

This application is a 371 National Stage Application of PCT/US2015/034435, filed Jun. 5, 2015, which claims the benefit of priority to U.S. Provisional Patent Application No. 62/008,715, filed Jun. 6, 2014, hereby incorporated by reference in their entirety.

GOVERNMENT INTEREST

This invention was made with government support under NS058830 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jun. 5, 2015, is named MSS-003.25 SL.txt and is 26,987 bytes in size.

BACKGROUND

Neurodegenerative diseases are characterized by a progressive neurodegenerative process in which neuron structure and/or function are lost over time. Among the most common and most severe neurodegenerative diseases are amyotrophic lateral sclerosis, Alzheimer's disease, Huntington's disease, and Parkinson's disease. Though genetic characteristics have been linked to some neurodegenerative diseases, the precise causes of most neurodegenerative diseases remain unclear. Further, effective treatments remain elusive for nearly all forms of neurodegenerative disease.

Parkinson's disease results from the death of dopamine-producing cells in the brain, and its primary motor symptoms arise from the loss of dopaminergic innervation in the striatum. The gold standard for treating Parkinson's is thus a neurotransmitter replacement strategy (levodopa, "L-DOPA") aimed at restoring dopaminergic signaling and improving motor function. The use of L-DOPA, however, frequently results in the formation of a series of severely debilitating hyperkinetic movements termed levodopa-induced dyskinesias (LIDs). The molecular etiology underlying LIDs is poorly understood. Although the discontinuous administration of levodopa is thought to be a triggering event, it remains unclear why certain individuals are refractory to the L-DOPA-mediated induction of dyskinesias.

SUMMARY

In some aspects, the invention relates to a method for treating a movement disorder in a subject in need thereof, comprising administering to the subject a therapeutically effective amount of a composition, wherein said composition reduces the activity of a nuclear receptor related 1 protein ("Nurr1"). In some embodiments, the movement disorder is a dyskinesia. The movement disorder may be a levodopa-induced dyskinesia.

In some embodiments, the composition comprises a nucleic acid molecule that encodes an interfering nucleic acid molecule. In certain embodiments, the interfering nucleic acid molecule is a short hairpin RNA. In other embodiments, the interfering nucleic acid molecule is a micro RNA. The interfering nucleic acid molecule may target Nurr1 mRNA for degradation.

In some aspects, the composition comprises a virus. The virus may be an adeno-associated virus ("AAV"), adenovirus, herpes simplex virus, or lentivirus. In some embodiments, the virus is AAV. In certain embodiments, the virus is AAV1. In some aspects, the genome of the virus comprises said nucleic acid molecule.

In certain aspects, the invention relates to compositions that comprise a nucleic acid molecule wherein the nucleic acid molecule is an interfering nucleic acid molecule. The interfering nucleic acid molecule may be an antisense molecule, a small interfering RNA molecule, a short hairpin RNA molecule, or a microRNA molecule. In some embodiments, the interfering nucleic acid molecule targets Nurr1 mRNA for degradation.

In certain embodiments, administering comprises inserting the composition at a desired location. The desired location may be the brain. In some embodiments, the desired location is the striatum. In certain embodiments, the desired location is the denervated striatum. Inserting may comprise injecting the composition.

In some embodiments, the subject is a mammal. The subject may be a primate, porcine, canine, ovine, or rodent. In certain embodiments, the subject is a human.

In some aspects, the invention relates to a method for treating levodopa-induced dyskinesia in a subject in need thereof, comprising administering to the subject a therapeutically effective amount of a composition. In certain aspects, the composition comprises a nucleic acid molecule that either is an interfering nucleic acid molecule or encodes an interfering nucleic acid molecule, administering comprises inserting the composition into the brain, and the composition reduces the activity of a nuclear receptor related 1 protein ("Nurr1").

BRIEF DESCRIPTION OF THE FIGURES

FIG. 1 depicts a vector containing a nucleotide sequence encoding a scrambled shRNA.

DETAILED DESCRIPTION

Overview

Approximately 50-80% of Parkinson's patients develop severely debilitating levodopa-induced dyskinesias (LIDs) that result in a significant reduction in their quality of life. While the pulsatile administration of dopamine enhancing drugs are thought to be important in the development of LIDs, a mechanism to explain how this occurs and why some patients remain LID resistant has yet to be identified. Without a clear mechanism to target for therapeutics, interventional strategies cannot be developed. In fact, clinicians are often limited to treating LIDs by reducing the dosage of levodopa, which exacerbates the primary motor symptoms of Parkinson's. Thus, there remains a great need for a pharmacological therapy that can reverse or prevent LIDs because such a therapy would allow patients to endure an uninterrupted course of levodopa. Further, the underlying associations between LIDs and other movement disorders (e.g. dystonias) suggests that a treatment for LIDs may prove useful in a number of other movement disorders.

To identify the differences between subjects who develop LIDs and those who do not, Sprague-Dawley rats were rendered parkinsonian using 6-hydroxydopamine, and their mRNA was screened to identify transcripts that were differentially expressed. The orphan nuclear receptor Nurr1 (nuclear receptor related 1 protein) was significantly elevated (greater than 30-fold) in LID-positive animals but not in LID-negative animals. This finding is striking because increasing Nurr1 activity has been proposed and studied in the context of neuroprotection. Additionally, prior reports suggest that Nurr1 is not normally expressed in the striatum.

The invention disclosed herein is based on the finding that Nurr1 expression correlates with the progression of LIDs, and the subsequent discovery that downregulating Nurr1 activity can slow the progression of LIDs.

Definitions

The articles "a" and "an" are used herein to refer to one or to more than one (i.e., to at least one) of the grammatical object of the article. By way of example, "an element" means one element or more than one element.

The term "activity" refers to the total capacity of a cell to perform a function. A treatment that decreases the activity of a nuclear receptor related 1 protein ("Nurr1") in a cell may reduce the amount of Nurr1 in a cell or reduce the efficiency of Nurr1. For example, a Nurr1 knockdown reduces the amount of Nurr1 in the cell. Additionally, mutations to the upstream regulators of Nurr1 may affect Nurr1 activity; for example, the knockdown of a transcription activator may decrease Nurr1 activity.

As used herein, the term "administering" means providing a pharmaceutical agent or composition to a subject, and includes, but is not limited to, administering by a medical professional and self-administering.

The term "encode" refers to nucleic acids that comprise a coding region, portion of a coding region, or compliments thereof. Both DNA and RNA may encode an interfering nucleic acid, an antisense nucleic acid molecule, a small interfering RNA molecule, a short hairpin RNA molecule, or a microRNA molecule.

The term "expression" refers to the amount of a nucleic acid or protein (e.g., peptide, polypeptide, etc.) in a cell. Expression of an interfering nucleic acid refers to the transcription of a nucleic acid that encodes the interfering nucleic acid. The expression of either a nucleic acid or a protein may be reduced. Decreased expression of a protein refers to the decreased translation of that protein. For example, an interfering nucleic acid may decrease the expression of Nurr1 by depleting the amount of Nurr1 mRNA that is available for translation.

The term "gene," as used herein, encompasses nucleotide sequences that encode amino acid sequences, including nucleotide sequences that did not derive from a genomic sequence. The term includes nucleotide sequences that are upstream or downstream of the coding sequence, such as regulatory regions, and it includes intron sequences.

As used herein, the term "interfering nucleic acid" is used generally to include a sequence of cyclic subunits, each bearing a base-pairing moiety, linked by intersubunit linkages that allow the base-pairing moieties to hybridize to a target sequence in a nucleic acid (typically RNA) by Watson-Crick base pairing, to form a nucleic acid:oligomer heteroduplex within the target sequence. Interfering RNA molecules include, but are not limited to, antisense molecules, siRNA molecules, single-stranded siRNA molecules, miRNA molecules, and shRNA molecules. Such interfering nucleic acids can be designed to block or inhibit the translation of mRNA or to inhibit natural pre-mRNA splice processing, or induce degradation of targeted mRNAs, and may be said to be "directed to" or "targeted against" a target sequence with which it hybridizes. Interfering nucleic acids may include, for example, peptide nucleic acids (PNAs), locked nucleic acids (LNAs), 2'-O-Methyl oligonucleotides and RNA interference agents (siRNA agents). RNAi molecules generally act by forming a heteroduplex with the target molecule, which is selectively degraded or "knocked down," hence inactivating the target RNA. Under some conditions, an interfering RNA molecule can also inactivate a target transcript by repressing transcript translation and/or inhibiting transcription of the transcript. An interfering nucleic acid is more generally said to be "targeted against" a biologically relevant target, such as a protein, when it is targeted against the nucleic acid of the target in the manner described above.

The terms "nucleic acid" refers to a polymeric form of nucleotides of any length, either deoxyribonucleotides or ribonucleotides, or analogs thereof. Polynucleotides may have any three-dimensional structure, and may perform any function. The following are non-limiting examples of polynucleotides: antisense nucleic acid molecules, small interfering RNA molecules, short hairpin RNA molecules, microRNA molecules, coding or non-coding regions of genes or gene fragments, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

The term "Nurr1" refers to "nuclear receptor related 1 protein," which is also known as "nuclear receptor subfamily 4, group A, member 2" (NR4A2). The sequences of the human Nurr1 gene and mRNA are shown in SEQ ID NO:2 and SEQ ID NO:1, respectively.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body.

The term "regulatory region" refers to nucleotide sequences that affect the transcription or translation of a gene but do not encode an amino acid sequence. Regulatory regions include promoters, operators, enhancers, and silencers.

An oligonucleotide "specifically hybridizes" to a target polynucleotide if the oligomer hybridizes to the target under physiological conditions, with a Tm substantially greater than 45° C., or at least 50° C., or at least 60° C.-80° C. or higher. Such hybridization corresponds to stringent hybridization conditions. At a given ionic strength and pH, the Tm is the temperature at which 50% of a target sequence hybridizes to a complementary polynucleotide. Again, such hybridization may occur with "near" or "substantial" complementarity of the antisense oligomer to the target sequence, as well as with exact complementarity.

As used herein, the term "subject" means a human or non-human animal selected for treatment or therapy. Subjects may include mammals, such as primates, porcine, canine, ovine, and rodentia.

The phrases "therapeutically-effective amount" and "effective amount" as used herein means the amount of an composition that is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

The term "treating" includes prophylactic and therapeutic treatments. The terms prophylactic and therapeutic are art-recognized and include the administration of one or more compositions to a subject. If the composition is administered prior to a clinical manifestation of an unwanted symptom or condition (e.g., before a subject develops LIDs) then the treatment is prophylactic (i.e., it protects the host against developing the unwanted condition), whereas if the composition is administered after manifestation of the unwanted condition (e.g., after a subject develops LIDs), the treatment is therapeutic, (i.e., it is intended to diminish, ameliorate, or stabilize the existing unwanted condition or side effects thereof). Thus, treating relates to the administration of a composition, such that at least one symptom of a condition is decreased or prevented from worsening in a subject or group of subjects relative to a subject or group of subjects who did not receive the composition; and treating also relates to the administration of a composition, such that the risk that a symptom will develop or worsen is diminished in a subject or group of subjects relative to a subject or group of subjects who did not receive the composition.

The term "vector" refers to the means by which a nucleic acid can be propagated and/or transferred between organisms, cells, or cellular components. Vectors include plasmids, linear DNA fragments, viruses, bacteriophage, pro-viruses, phagemids, transposons, and artificial chromosomes, and the like, that may or may not be able to replicate autonomously or integrate into a chromosome of a host cell. Additionally, the term vector refers to exogenous nucleotide sequences from plasmids, linear DNA fragments, viruses, bacteriophage, pro-viruses, phagemids, transposons, and artificial chromosomes, and the like, a that have integrated into an organism's genome.

A. Interfering Nucleic Acids

In certain embodiments, interfering nucleic acid molecules that selectively target Nurr1 are provided herein and/or used in methods described herein. Interfering nucleic acids generally include a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence. Interfering RNA molecules include, but are not limited to, antisense molecules, siRNA molecules, single-stranded siRNA molecules, miRNA molecules and shRNA molecules.

Typically at least 17, 18, 19, 20, 21, 22 or 23 nucleotides of the complement of the target mRNA sequence are sufficient to mediate inhibition of a target transcript. Perfect complementarity is not necessary. In some embodiments, the interfering nucleic acid molecule is double-stranded RNA. The double-stranded RNA molecule may have a 2 nucleotide 3' overhang. In some embodiments, the two RNA strands are connected via a hairpin structure, forming a shRNA molecule. shRNA molecules can contain hairpins derived from microRNA molecules. For example, an RNAi vector can be constructed by cloning the interfering RNA sequence into a pCAG-miR30 construct containing the hairpin from the miR30 miRNA. RNA interference molecules may include DNA residues, as well as RNA residues.

Interfering nucleic acid molecules provided herein can contain RNA bases, non-RNA bases or a mixture of RNA bases and non-RNA bases. For example, interfering nucleic acid molecules provided herein can be primarily composed of RNA bases but also contain DNA bases or non-naturally occurring nucleotides.

The interfering nucleic acids can employ a variety of oligonucleotide chemistries. Examples of oligonucleotide chemistries include, without limitation, peptide nucleic acid (PNA), linked nucleic acid (LNA), phosphorothioate, 2'O-Me-modified oligonucleotides, and morpholino chemistries, including combinations of any of the foregoing. In general, PNA and LNA chemistries can utilize shorter targeting sequences because of their relatively high target binding strength relative to 2'O-Me oligonucleotides. Phosphorothioate and 2'O-Me-modified chemistries are often combined to generate 2'O-Me-modified oligonucleotides having a phosphorothioate backbone (See, e.g., PCT Publication Nos. WO/2013/112053; U.S. Pat. No. 8,609,065, incorporated by reference).

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm, Buchardt et al., Nature, 365:566-68 (1993)). The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases.

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. Panagene has developed proprietary benzothiazole-2-sulfonyl-PNA monomers (Bts PNA) and proprietary oligomerization processes. The PNA oligomerization using Bts PNA monomers is composed of repetitive cycles of deprotection, coupling and capping. PNAs can be produced synthetically using any technique known in the art (See, e.g., U.S. Pat. Nos. 6,969,766, 7,211,668, 7,022,851, 7,125,994, 7,145,006 and 7,179,896, which are incorporated by reference. See also U.S. Pat. Nos. 5,539,082; 5,714,331; and 5,719,262 for the preparation of PNAs, which are incorporated by reference). Further teaching of PNA compounds can be found in Nielsen et al., Science, 254:1497-1500 (1991).

Interfering nucleic acids may also contain "locked nucleic acid" subunits (LNAs). "LNAs" are a member of a class of modifications called bridged nucleic acid (BNA). BNA is characterized by a covalent linkage that locks the conformation of the ribose ring in a C30-endo (northern) sugar pucker. For LNA, the bridge is composed of a methylene between the 2'-O and the 4'-C positions. LNA enhances backbone preorganization and base stacking to increase hybridization and thermal stability.

The structures of LNAs can be found, for example, in Chemical Communications, 455-56 (1998); Tetrahedron, 54:3607 (1998); Accounts Chemical Research, 32:301 (1999); Tetrahedron Letters, 38:8735-38 (1997); Tetrahedron Letters, 39:5401-04 (1998); and Bioorganic Medicinal Chemistry, 16:9230-37 (2008).

Compounds provided herein may incorporate one or more LNAs; in some cases, the compounds may be entirely composed of LNAs. Methods for the synthesis of individual LNA nucleoside subunits and their incorporation into oligonucleotides are described, for example, in U.S. Pat. Nos. 7,572,582, 7,569,575, 7,084,125, 7,060,809, 7,053,207, 7,034,133, 6,794,499, and 6,670,461, each of which is incorporated by reference. Typical intersubunit linkers include phosphodiester and phosphorothioate moieties; alternatively, non-phosphorous containing linkers may be employed. One embodiment is an LNA containing compound where each LNA subunit is separated by a DNA subunit. Certain compounds are composed of alternating LNA and DNA subunits where the intersubunit linker is phosphorothioate.

"Phosphorothioates" (or S-oligos) are a variant of normal DNA in which one of the nonbridging oxygens is replaced by a sulfur. The sulfurization of the internucleotide bond reduces the action of endo-and exonucleases including 5' to 3' and 3' to 5' DNA POL 1 exonuclease, nucleases S1 and P1, RNases, serum nucleases and snake venom phosphodiesterase. Phosphorothioates are made by two principal routes: by the action of a solution of elemental sulfur in carbon disulfide on a hydrogen phosphonate, or by the method of sulfurizing phosphite triesters with either tetraethylthiuram disulfide (TETD) or 3H-1, 2-bensodithiol-3-one 1, 1-dioxide (BDTD) (See, e.g., Iyer et al., J. Organic Chemistry 55:4693-4699 (1990)). The latter methods avoid the problem of elemental sulfur's insolubility in most organic solvents and the toxicity of carbon disulfide. The TETD and BDTD methods also yield higher purity phosphorothioates.

"2'O-Me oligonucleotides" molecules carry a methyl group at the 2'-OH residue of the ribose molecule. 2'-O-Me-RNAs show the same (or similar) behavior as DNA, but are protected against nuclease degradation. 2'-O-Me-RNAs can also be combined with phosphothioate oligonucleotides (PTOs) for further stabilization. 2'O-Me oligonucleotides (phosphodiester or phosphothioate) can be synthesized according to routine techniques in the art (See, e.g., Yoo et al., Nucleic Acids Research 32:2008-16 (2004)).

The interfering nucleic acids described herein may be contacted with a cell or administered to an organism (e.g., a human). Alternatively, constructs and/or vectors encoding the interfering RNA molecules may be contacted with or introduced into a cell or organism. In certain embodiments, a viral vector is used. The viral vector may be an adenovirus vector; an adeno-associated virus vector; a pox virus vector, such as a fowlpox virus vector; an alpha virus vector; a bacloviral vector; a herpes virus vector; a retrovirus vector, such as a lentivirus vector; a Modified Vaccinia virus Ankara vector; a Ross River virus vector; a Sindbis virus vector; a Semliki Forest virus vector; and a Venezuelan Equine Encephalitis virus vector. In some embodiments, the vector has a tropism for neural tissue. In some embodiments the vector is an adeno-associated virus.

Typically at least 17, 18, 19, 20, 21, 22 or 23 nucleotides of the complement of the target mRNA sequence are sufficient to mediate inhibition of a target transcript. Perfect complementarity is not necessary. In some embodiments, the interfering nucleic acids contains a 1, 2 or 3 nucleotide mismatch with the target sequence. The interfering nucleic acid molecule may have a 2 nucleotide 3' overhang. If the interfering nucleic acid molecule is expressed in a cell from a construct, for example from a hairpin molecule or from an inverted repeat of the desired sequence, then the endogenous cellular machinery will create the overhangs. shRNA molecules can contain hairpins derived from microRNA molecules. For example, an RNAi vector can be constructed by cloning the interfering RNA sequence into a pCAG-miR30 construct containing the hairpin from the miR30 miRNA. RNA interference molecules may include DNA residues, as well as RNA residues.

In some embodiments, the interfering nucleic acid molecule is a siRNA molecule. Such siRNA molecules should include a region of sufficient homology to the target region, and be of sufficient length in terms of nucleotides, such that the siRNA molecule down-regulate target RNA. The term "ribonucleotide" or "nucleotide" can, in the case of a modified RNA or nucleotide surrogate, also refer to a modified nucleotide, or surrogate replacement moiety at one or more positions. It is not necessary that there be perfect complementarity between the siRNA molecule and the target, but the correspondence must be sufficient to enable the siRNA molecule to direct sequence-specific silencing, such as by RNAi cleavage of the target RNA. In some embodiments, the sense strand need only be sufficiently complementary with the antisense strand to maintain the overall double-strand character of the molecule.

In addition, an siRNA molecule may be modified or include nucleoside surrogates. Single stranded regions of an siRNA molecule may be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of an siRNA molecule, e.g., against exonucleases, or to favor the antisense siRNA agent to enter into RISC are also useful. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

Each strand of an siRNA molecule can be equal to or less than 35, 30, 25, 24, 23, 22, 21, or 20 nucleotides in length. In some embodiments, the strand is at least 19 nucleotides in length. For example, each strand can be between 21 and 25 nucleotides in length. In some embodiments, siRNA agents have a duplex region of 17, 18, 19, 29, 21, 22, 23, 24, or 25 nucleotide pairs, and one or more overhangs, such as one or two 3' overhangs, of 2-3 nucleotides.

Suitable siRNA nucleotide sequences for decreasing Nurr1 activity include SEQ ID NOs.: 3, 5, 7, and 9-12, and those with ordinary skill in the art will recognize that many other nucleotide sequences may be designed to decrease Nurr1 activity.

A "small hairpin RNA" or "short hairpin RNA" or "shRNA" includes a short RNA sequence that makes a tight hairpin turn that can be used to silence gene expression via RNA interference. The shRNAs provided herein may be chemically synthesized or transcribed from a transcriptional cassette in a DNA plasmid. The shRNA hairpin structure is cleaved by the cellular machinery into siRNA, which is then bound to the RNA-induced silencing complex (RISC).

In some embodiments, shRNAs are about 15-60, 15-50, or 15-40 (duplex) nucleotides in length, about 15-30, 15-25, or 19-25 (duplex) nucleotides in length, or are about 20-24, 21-22, or 21-23 (duplex) nucleotides in length (e.g., each complementary sequence of the double-stranded shRNA is 15-60, 15-50, 15-40, 15-30, 15-25, or 19-25 nucleotides in length, or about 20-24, 21-22, or 21-23 nucleotides in length, and the double-stranded shRNA is about 15-60, 15-50, 15-40, 15-30, 15-25, or 19-25 base pairs in length, or about 18-22, 19-20, or 19-21 base pairs in length). shRNA duplexes may comprise 3' overhangs of about 1 to about 4 nucleotides or about 2 to about 3 nucleotides on the antisense strand and/or 5'-phosphate termini on the sense strand. In some embodiments, the shRNA comprises a sense strand and/or antisense strand sequence of from about 15 to about 60 nucleotides in length (e.g., about 15-60, 15-55, 15-50, 15-45, 15-40, 15-35, 15-30, or 15-25 nucleotides in length), or from about 19 to about 40 nucleotides in length (e.g., about 19-40, 19-35, 19-30, or 19-25 nucleotides in length), or from about 19 to about 23 nucleotides in length (e.g., 19, 20, 21, 22, or 23 nucleotides in length).

Non-limiting examples of shRNA include a double-stranded polynucleotide molecule assembled from a single-stranded molecule, where the sense and antisense regions are linked by a nucleic acid-based or non-nucleic acid-based linker; and a double-stranded polynucleotide molecule with a hairpin secondary structure having self-complementary sense and antisense regions. In some embodiments, the sense and antisense strands of the shRNA are linked by a loop structure comprising from about 1 to about 25 nucleotides, from about 2 to about 20 nucleotides, from about 4 to about 15 nucleotides, from about 5 to about 12 nucleotides, or 1, 2, 3, 4, 5, 6, 7, 8, 9, 10, 11, 12, 13, 14, 15, 16, 17, 18, 19, 20, 21, 22, 23, 24, 25, or more nucleotides.

Additional embodiments related to the shRNAs, as well as methods of designing and synthesizing such shRNAs, are described in U.S. patent application publication number 2011/0071208, which is herein incorporated by reference.

Suitable shRNA nucleotide sequences for decreasing Nurr1 activity are shown in SEQ ID NOs. 4, 6, 8, and 13, and those with ordinary skill in the art will recognize that many other nucleotide sequences may be designed to decrease Nurr1 activity.

In some embodiments, provided herein are micro RNAs (miRNAs). miRNAs represent a large group of small RNAs produced naturally in organisms, some of which regulate the expression of target genes. miRNAs are formed from an approximately 70 nucleotide single-stranded hairpin precursor transcript by Dicer. miRNAs are not translated into proteins, but instead bind to specific messenger RNAs, thereby blocking translation. In some instances, miRNAs base-pair imprecisely with their targets to inhibit translation.

In some embodiments, antisense oligonucleotide compounds are provided herein. In certain embodiments, the degree of complementarity between the target sequence and antisense targeting sequence is sufficient to form a stable duplex. The region of complementarity of the antisense oligonucleotides with the target RNA sequence may be as short as 8-11 bases, but can be 12-15 bases or more, e.g., 10-40 bases, 12-30 bases, 12-25 bases, 15-25 bases, 12-20 bases, or 15-20 bases, including all integers in between these ranges. An antisense oligonucleotide of about 14-15 bases is generally long enough to have a unique complementary sequence.

In certain embodiments, antisense oligonucleotides may be 100% complementary to the target sequence, or may include mismatches, e.g., to improve selective targeting of allele containing the disease-associated mutation, as long as a heteroduplex formed between the oligonucleotide and target sequence is sufficiently stable to withstand the action of cellular nucleases and other modes of degradation which may occur in vivo. Hence, certain oligonucleotides may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligonucleotide and the target sequence. Oligonucleotide backbones that are less susceptible to cleavage by nucleases are discussed herein. Mismatches, if present, are typically less destabilizing toward the end regions of the hybrid duplex than in the middle. The number of mismatches allowed will depend on the length of the oligonucleotide, the percentage of G:C base pairs in the duplex, and the position of the mismatch(es) in the duplex, according to well understood principles of duplex stability.

Interfering nucleic acid molecules can be prepared, for example, by chemical synthesis, in vitro transcription, or digestion of long dsRNA by Rnase III or Dicer. These can be introduced into cells by transfection, electroporation, or other methods known in the art (See Hannon, Nature, 418:244-51 (2002); Bernstein et al., RNA, 7:1509-21 (2002); Hutvagner et al., Current Opinion Genetics & Development, 12:225-32 (2002); Brummelkamp, Science, 296:550-53 (2002); Lee et al., Nature Biotechnology, 20:500-05 (2002); Miyagishi & Taira, Nature Biotechnology, 20:497-00 (2002); Paddison et al., Genes & Development, 16:948-58 (2002); Paul et al., Nature Biotechnology, 20:505-08 (2002); Sui et al., Proceedings Nat'l Academy Sci. USA, 99:5515-20 (2002); Yu et al., Proceedings Nat'l Academy Sci. USA, 99:6047-52 (2002)).

In the present methods, an interfering nucleic acid molecule or an interfering nucleic acid encoding polynucleotide can be administered to the subject, for example, as naked nucleic acid, in combination with a delivery reagent, and/or as a nucleic acid comprising sequences that express an interfering nucleic acid molecule. In some embodiments the nucleic acid comprising sequences that express the interfering nucleic acid molecules are delivered within vectors, e.g. plasmid, viral and bacterial vectors. Any nucleic acid delivery method known in the art can be used in the methods described herein. Suitable delivery reagents include, but are not limited to, e.g., the Minis Transit TKO lipophilic reagent; lipofectin; lipofectamine; cellfectin; polycations (e.g., polylysine), atelocollagen, nanoplexes and liposomes. The use of atelocollagen as a delivery vehicle for nucleic acid molecules is described in Minakuchi et al. Nucleic Acids Research, 32:e109 (2004); Hanai et al. Annals N.Y. Acad. Sci., 1082:9-17 (2006); Kawata et al. Molecular Cancer Therapeutics, 7:2904-12 (2008). Exemplary interfering nucleic acid delivery systems are provided in U.S. Pat. Nos. 8,283,461, 8,313,772, 8,501,930. 8,426,554, 8,268,798 and 8,324,366, each of which is hereby incorporated by reference.

B. Viral Vectors

1. Adeno-Associated Virus

The nucleic acids of the invention can be delivered to the cells of the central nervous system by using viral vectors or by using non-viral vectors. The use of AAV vectors to deliver interfering nucleic acids into the brain is well known in the art (See, e.g., U.S. Pat. No. 8,487,088, incorporated by reference). In certain embodiments, the invention uses adeno-associated viral (AAV) vectors comprising the a nucleotide sequence encoding an interfering nucleic acid.

The use of AAV vectors to deliver interfering nucleic acids is well known in the art (Borel et al., Molecular Therapy, 22:692-01 (2013)). Additionally, those with skill in the art know that AAV vectors may be used to deliver nucleotide sequences to the brain (Kaplitt et al., Lancet, 369:2097-05 (2007); U.S. Patent Application Publication No. 2013/0224836, incorporated by reference).

AAV vectors can be constructed using known techniques to provide at least the operatively linked components of control elements including a transcriptional initiation region, a exogenous nucleic acid molecule, a transcriptional termination region and at least one post-transcriptional regulatory sequence. The control elements are selected to be functional in the targeted cell. The resulting construct which contains the operatively linked components is flanked at the 5' and 3' region with functional AAV inverted terminal repeat sequences (ITRs).

The nucleotide sequences of AAV ITR regions are known. The ITR sequences for AAV-2 are described, for example, by Kotin et al., Human Gene Therapy, 5:793-01 (1994); Fields & Knipe, *Fundamental Virology*, "Parvoviridae and their Replication" (2d ed. 1986). The skilled artisan will appreciate that AAV ITR's can be modified using standard molecular biology techniques (e.g., Green & Sambrook, *Molecular Cloning: A Laboratory Manual*, (4th ed., 2012)). Accordingly, AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including but not limited to, AAV-1, AAV-2, AAV-3, AAV-4, AAV-5, AAV-7, and the like. Furthermore, the 5' and 3' ITRs, which flank a selected nucleotide sequence in an AAV expression vector, need not necessarily be identical or derived from the same AAV serotype or isolate, so long as the ITR's function as intended, i.e., to allow for excision and replication of the bounded nucleotide sequence of interest when AAV rep gene products are present in the cell.

The skilled artisan can appreciate that regulatory sequences can often be provided from commonly used promoters derived from viruses such as, polyoma, Adenovirus 2, cytomegalovirus and Simian Virus 40. Use of viral regulatory elements to direct expression of the protein can allow for high level constitutive expression of the protein in a variety of host cells. Ubiquitously expressing promoters can also be used include, for example, the early cytomegalovirus promoter (Boshart et al., Cell, 41:521-30 (1985)), herpesvirus thymidine kinase promoter (McKnight et al. Cell, 37: 253-62 (1984)), β-actin promoters (e.g., the human β-actin promoter, Ng et al., Molecular Cell Biology, 5:2720-32(1985)), and colony stimulating factor-1 promoter (Ladner et al., EMBO J., 6:2693-98(1987)).

Alternatively, the regulatory sequences of the AAV vector can direct expression of the gene preferentially in a particular cell type, i.e., tissue-specific regulatory elements can be used. Non-limiting examples of tissue-specific promoters which can be used include, central nervous system (CNS) specific promoters such as, neuron-specific promoters (e.g, the neurofilament promoter; Byrne and Ruddle, Proceedings Nat'l Acad. Sci. USA, 86:5473-77 (1989)) and glial specific promoters (Morii et al., Biochemical & Biophysical Research Communications, 175:185-91 (1991)). Preferably, the promoter is tissue specific and is essentially not active outside the central nervous system, or the activity of the promoter is higher in the central nervous system that in other systems. For example, a promoter specific for the spinal cord, brainstem, (medulla, pons, and midbrain), cerebellum, diencephalon (thalamus, hypothalamus), telencephalon (corpus stratium, cerebral cortex, or within the cortex, the occipital, temporal, parietal or frontal lobes), or combinations, thereof. The promoter may be specific for particular cell types, such as neurons or glial cells in the CNS. If it is active in glial cells, it may be specific for astrocytes, oligodentrocytes, ependymal cells, Schwann cells, or microglia. If it is active in neurons, it may be specific for particular types of neurons, e.g., motor neurons, sensory neurons, or interneurons. Preferably, the promoter is specific for cells in particular regions of the brain, for example, the cortex, stratium, nigra and hippocampus.

Suitable neuronal specific promoters include, but are not limited to, neuron specific enolase (NSE) (Olivia et al., Genomics, 10:157-65 (1991), GenBank Accession No: X51956), and human neurofilament light chain promoter (NEFL) (Rogaev et al., Human Molecular Genetics, 1:781 (1992), GenBank Accession No: L04147). Glial specific promoters include, but are not limited to, glial fibrillary acidic protein (GFAP) promoter (Morii et al., Biochemical & Biophysical Research Communications, 175:185-91 (1991), GenBank Accession No:M65210), S100 promoter (Morii et al., Biochemical & Biophysical Research Communications, 175:185-91 (1991), GenBank Accession No: M65210) and glutamine synthase promoter (Van den et al., Biochimica Biophysica Acta, 2:249-51(1991), GenBank Accession No: X59834). In a preferred embodiment, the gene is flanked upstream (i.e., 5') by the neuron specific enolase (NSE) promoter. In another preferred embodiment, the gene of interest is flanked upstream (i.e., 5') by the elongation factor 1 alpha (EF) promoter.

Suitable promoters for expressing an interfering nucleic acid include RNA polymerase III promoters such as the H1 promoter or the U6 promoter. (See, e.g., U.S. Pat. No. 7,985,581; U.S. Pat. No. 8,283,461, incorporated by reference).

The AAV vector harboring the nucleotide sequence of interest, e.g., the sequence encoding an interfering nucleic acid, and a post-transcriptional regulatory sequence (PRE) flanked by AAV ITRs, can be constructed by directly inserting the nucleotide sequence of interest and the PRE into an AAV genome which has had the major AAV open reading frames ("ORFs") excised therefrom. Other portions of the AAV genome can also be deleted, as long as a sufficient portion of the ITRs remain to allow for replication and packaging functions. These constructs can be designed using techniques well known in the art. (See, e.g., Lebkowski et al., Molecular & Cellular Biology, 8:3988-96 (1988); Vincent et al., Vaccines 90 (Cold Spring Harbor Laboratory Press, 1990); Carter, Current Opinion Biotechnology, 3:533-39 (1992); Muzyczka, Current Topics Microbiology & Immunology, 158:97-29 (1992); Kotin, Human Gene Therapy, 5:793-01(1994); Shelling et al., Gene Therapy, 1:165-69 (1994); and Zhou et al., J Experimental Medicine, 179:1867-75 (1994)). Alternatively, AAV ITRs can be excised from the viral genome or from an AAV vector containing the same and fused 5' and 3' of a selected nucleic acid construct that is present in another vector using standard ligation techniques, such as those described in Green & Sambrook (Green & Sambrook, *Molecular Cloning: A Laboratory Manual*, (4th ed., 2012)). Several AAV vectors are available from the American Type Culture Collection ("ATCC") under Accession Numbers 53222, 53223, 53224, 53225 and 53226.

In order to produce recombinant AAV particles, an AAV vector can be introduced into a suitable host cell using known techniques, such as by transfection. A number of transfection techniques are generally known in the art (See, e.g., Graham et al., Virology, 52:456 (1973); Green & Sambrook, *Molecular Cloning: A Laboratory Manual*, (4th ed., 2012); Davis et al., Basic Methods Molecular Biology, (Elsevier, 1986); and Chu et al., Gene, 13:197 (1981)). Particularly suitable transfection methods include calcium phosphate co-precipitation (Graham et al., Virology, 52:456-67 (1973)), direct microinjection into cultured cells (Capecchi, Cell, 22:479-88 (1980)), electroporation (Shigekawa et al., BioTechniques, 6:742-51 (1988)), liposome mediated gene transfer (Mannino et al., BioTechniques, 6:682-90 (1988)), lipid-mediated transduction (Feigner et al., Proceedings Nat'l Acad. Sci. USA, 84:7413-17(1987)), and nucleic acid delivery using high-velocity microprojectiles (Klein et al., Nature 327:70-73 (1987)).

Suitable host cells for producing recombinant AAV particles include, but are not limited to, microorganisms, yeast cells, insect cells, and mammalian cells, that can be, or have been, used as recipients of a exogenous nucleic acid molecule. Thus, a "host cell" as used herein generally refers to a cell which has been transfected with an exogenous nucleic acid molecule. The host cell includes any eukaryotic cell or cell line so long as the cell or cell line is not incompatible with the protein to be expressed, the selection system chosen or the fermentation system employed. Non-limiting examples include CHO DHFR-minus cells (Urlaub and Chasin Proceedings Nat'l Acad. Sci. USA, 77:4216-420 (1980)), 293 cells (Graham et al., J. General Virology 36:59-72 (1977)), or myeloma cells like SP2 or NSO (Galfre & Milstein, Methods Enzymology, 73:3-46 (1981)).

In one embodiment, cells from the stable human cell line, 293 (readily available through, e.g., the ATCC under Accession No. ATCC CRL1573). Particularly, the human cell line 293, which is a human embryonic kidney cell line that has been transformed with adenovirus type-5 DNA fragments (Graham et al., J. General Virology, 36:59-72 (1977)), and expresses the adenoviral E1a and E1b genes (Aiello et al., Virology, 94:460-69 (1979)). The 293 cell line is readily transfected, and provides a particularly convenient platform in which to produce AAV virions.

Host cells containing the above-described AAV vectors must be rendered capable of providing AAV helper functions in order to replicate and encapsidate the expression cassette flanked by the AAV ITRs to produce recombinant AAV particles. AAV helper functions are generally AAV-derived coding sequences which can be expressed to provide AAV gene products that, in turn, function in trans for productive AAV replication. AAV helper functions are used herein to complement necessary AAV functions that are missing from the AAV vectors. Thus, AAV helper functions include one, or both of the major AAV open reading frames (ORFs), namely the rep and cap coding regions, or functional homologues thereof.

The AAV rep coding region of the AAV genome encodes the replication proteins Rep 78, Rep 68, Rep 52, and Rep 40. These Rep expression products have been shown to possess many functions, including recognition, binding and nicking of the AAV origin of DNA replication, DNA helicase activity and modulation of transcription from AAV (or other exogenous) promoters. The Rep expression products are collectively required for replicating the AAV genome. The AAV cap coding region of the AAV genome encodes the capsid proteins VP1, VP2, and VP3, or functional homologues thereof. AAV helper functions can be introduced into the host cell by transfecting the host cell with an AAV helper construct either prior to, or concurrently with, the transfection of the AAV vector comprising the expression cassette, AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products (See, e.g., Samulski et al., J. Virology, 63:3822-28 (1989); McCarty et al., J. Virology, 65:2936-45 (1991)). A number of other vectors have been described which encode Rep and/or Cap expression products (See, e.g., U.S. Pat. No. 5,139,941, incorporated by reference).

As a consequence of the infection of the host cell with a helper virus, the AAV Rep and/or Cap proteins are produced. The Rep proteins also serve to duplicate the AAV genome. The expressed Cap proteins assemble into capsids, and the AAV genome is packaged into the capsids. This results the AAV being packaged into recombinant AAV particles comprising the expression cassette. Following recombinant AAV replication, recombinant AAV particles can be purified from the host cell using a variety of conventional purification methods, such as CsCl gradients. The resulting recombinant AAV particles are then ready for use for gene delivery to various cell types.

In one embodiment, the number of viral vector and/or virion particles administered to a mammal may be on the order ranging from $10^3$ to $10^{15}$ particles/ml, or any values therebetween, such as for example, about $10^5$, $10^6$, $10^7$, $10^8$, $10^9$, $10^{10}$, $10^{11}$, $10^{12}$, $10^{13}$, $10^{14}$, or $10^{15}$ particles/ml. In one embodiment, vector and/or virion particles of higher than $10^{13}$ particles/ml are administered. Volumes between 1 µl and 10 ml may be administered such that the subject receives between $10^3$ and $10^{16}$ total vector and/or virion particles. Thus, in some embodiments, about $10^5$, $10^6$, $10^7$, $10^8$, $10^9$, $10^{10}$, $10^{11}$, $10^{12}$, $10^{13}$, $10^{14}$, $10^{15}$, or $10^{16}$ vector and/or virion particles are administered.

In certain instances, the AAV serotype is selected from AAV1, AAV2, AAV3, AAV4, AAV5, AAV6, AAV6.2, AAV7, AAV8, AAV9, rh.10, rh.39, rh.43, and CSp3.

Alternatively, a vector of the invention can be a virus other than the adeno-associated virus, or portion thereof, which allows for expression of a nucleic acid molecule introduced into the viral nucleic acid. For example, replication defective retroviruses, adenoviruses, herpes simplex viruses, and lentivirus can be used. Protocols for producing recombinant retroviruses and for infecting cells in vitro or in vivo with such viruses can be found in Ausubel et al., Current Protocols in Molecular Biology §§ 9.10-9.14 (Greene Publishing Associates, 1989) and other standard laboratory manuals. Examples of suitable retroviruses include pLJ, pZIP, pWE and pEM, which are well known to those skilled in the art. Examples of suitable packaging virus lines include Crip, Cre, 2 and Am. The genome of adenovirus can be manipulated such that it encodes and expresses the protein of interest but is inactivated in terms of its ability to replicate in a normal lytic viral life cycle (See e.g., Berkner et al., BioTechniques, 6:616-29 (1988); Rosenfeld et al., Science, 252:431-34 (1991); Rosenfeld et al., Cell 68:143-55 (1992)). Suitable adenoviral vectors derived from the adenovirus strain Ad type 5 dl324 or other strains of adenovirus (e.g., Ad2, Ad3, Ad7 etc.) are well known to those skilled in the art.

2. Lentivirus

Lentiviral vectors may be utilized to express interfering nucleic acids in the nervous system, and the production of suitable lentiviral vectors is well known in the art (See, e.g., U.S. Patent Application Publication No. 2013/0281975, incorporated by reference). The lentiviral vector according to the present invention may be derived from or may be derivable from any suitable lentivirus. A recombinant lentiviral particle is capable of transducing a target cell with a nucleotide of interest. Once within the cell the RNA genome from, the vector particle is reverse transcribed into DNA and integrated into the genome of the target cell.

Lentiviral vectors are part of a larger group of retroviral vectors. A detailed list of lentiviruses may be found in Coffin et al., Retroviruses 758-763 (Cold Spring Harbor Laboratory Press, 1997). In brief, lentiviruses can be divided into primate and non-primate groups. Examples of primate lentiviruses include but are not limited to the human immunodeficiency virus (HIV) and the simian immunodeficiency virus (SrV). The non-primate lentiviral group includes the prototype "slow virus" visna/maedi virus (VMV), as well as the related caprine arthritis-encephalitis virus (CAEV), equine infectious anemia virus (EIAV), feline immunodeficiency virus (FIV), bovine immunodeficiency virus (BIV).

Lentiviruses differ from other members of the retrovirus family in that lentiviruses have the capability to infect both dividing and non-dividing cells (Lewis et al., EMBO J., 11:3053-58 (1992)); Lewis & Emerman, J Virology, 68:510-16 (1994)). In contrast, other retroviruses, such as MLV, are unable to infect non-dividing or slowly dividing cells such as those that make up, for example, muscle, brain, lung and liver tissue.

A lentiviral vector, as used herein, is a vector which comprises at least one component part derivable from a lentivirus. That component part may be involved in the biological mechanisms by which the vector infects cells, expresses genes or is replicated. The basic structure of retrovirus and lentivirus genomes share many common features such as a 5' LTR and a 3' LTR, between or within which are located a packaging signal to enable the genome to be packaged, a primer binding site, integration sites to enable integration into a host cell genome and gag, pol and env genes encoding the packaging components, which are polypeptides required for the assembly of viral particles. Lentiviruses have additional features, such as the rev and rev response element (RRE) sequences, which enable the efficient export of RNA transcripts of the integrated provirus from the nucleus to the cytoplasm of an infected target cell. In the provirus, the viral genes are flanked at both ends by regions called long terminal repeats (LTRs). The LTRs are responsible for proviral integration, and transcription. LTRs also serve as enhancer-promoter sequences and can control the expression of the viral genes. The LTRs themselves are identical sequences that can be divided into three elements, which are called "U3," "R" and "U5." U3 is derived from the sequence unique to the 3' end of the RNA, R is derived from a sequence repeated at both ends of the RNA, and U5 is derived from the sequence unique to the 5' end of the RNA. The sizes of the three elements can vary considerably among different viruses.

In a defective lentiviral vector genome gag, pol and env may be absent or non-functional. The R regions at both ends of the RNA are repeated sequences. U5 and U3 represent unique sequences at the 5' and 3' ends of the RNA genome respectively.

In a typical lentiviral vector of the present invention, at least part of one or more protein coding regions essential for replication may be removed from the virus, which makes the viral vector replication-defective. Portions of the viral genome may also be replaced by an interfering nucleic acid in order to generate a vector comprising an interfering nucleic acid which is capable of transducing a target non-dividing host cell and/or integrating its genome into a host genome. In one embodiment, the lentiviral vectors are non-integrating vectors as described in U.S. Patent Application Publication No. 2009/0017543 (herein incorporated by reference).

In a further embodiment, the vectors have the ability to deliver a sequence which is devoid of or lacking viral RNA. A heterologous binding domain (heterologous to gag) may be located on the RNA to be delivered and a cognate binding domain on gag or pol can be used to ensure packaging of the RNA to be delivered. Both of these vectors are described in U.S. Patent Application Publication No. 2009/0075370 (herein incorporated by reference). The lentiviral vector may be a "non-primate" vector, i.e., derived from a virus which does not primarily infect primates, especially humans.

The examples of non-primate lentivirus may be any member of the family of lentiviridae which does not naturally infect a primate and may include a feline immunodeficiency virus (FIV), a bovine immunodeficiency virus (BIV), a caprine arthritis encephalitis virus (CAEV), a Maedi-visna virus (MW) or an equine infectious anemia virus (EIAV).

In some embodiments, the viral vector is derived from EIAV. EIAV has the simplest genomic structure of the lentiviruses. In addition to the gag, pol and env genes, EIAV encodes three other genes: tat, rev, and S2. Tat acts as a transcriptional activator of the viral LTR (Derse & Newbold, Virology, 194:530-36(1993); Maury et al., Virology, 200: 632-42(1994)). Rev regulates and coordinates the expression of viral genes through rev-response elements (RRE) (Martarano et al., J. Virology, 68:3102-11 (1994)). The mechanisms of action of these two proteins are thought to be broadly similar to the analogous mechanisms in the primate viruses (Martarano et al., J. Virology, 68:3102-11 (1994)). The function of S2 is unknown. In addition, an EIAV protein, Ttm, has been identified that is encoded by the first exon of tat spliced to the env coding sequence at the start of the transmembrane protein.

The viral vector may be manipulated to remove the non-essential elements and to retain the essential elements in order to provide the required functionality to infect, transduce and deliver a nucleotide sequence of interest to a target host cell (See, e.g., U.S. Pat. No. 6,669,936, incorporated by reference). In some embodiments, the genome is limited to sufficient lentiviral genetic information to allow packaging of an RNA genome, in the presence of packaging components, into a viral particle capable of infecting a target cell. Infection of the target cell may include reverse transcription and integration into the target cell genome. The lentiviral vector carries non-viral coding sequences which are to be delivered by the vector to the target cell. In some embodiments, the vector is incapable of independent replication to produce infectious lentiviral particles within the final target cell. Usually the recombinant lentiviral vector lacks a functional gag-pol and/or env gene and/or other genes essential for replication. The vector of the present invention may be configured as a split-intron vector (See, e.g., U.S. Pat. No. 7,303,910, incorporated by reference).

The vector may be a self-inactivating vector. Self-inactivating retroviral vectors may be constructed by deleting the transcriptional enhancers or the enhancers and promoter in the U3 region of the 3' LTR. After a round of vector reverse transcription and integration, these changes are copied into both the 5' and the 3' LTRs producing a transcriptionally inactive provirus (Yu et al., Proceedings Nat'l Acad. Sci. USA, 83:3194-98 (1986); Dougherty and Temin et al., Proceedings Nat'l Acad. Sci. USA, 84:1197-01 (1987); Hawley, Proceedings Nat'l Acad. Sci. USA, 84:2406-10 (1987); Yee et al., Proceedings Nat'l Acad. Sci. USA, 91:9564-68 (1994)). However, any promoter(s) internal to the LTRs in such vectors will still be transcriptionally active. This strategy has been employed to eliminate effects of the enhancers and promoters in the viral LTRs on transcription from internally placed genes. Such effects include increased transcription (Jolly et al., Nucleic Acids Research, 11:1855-72 (1983)) or suppression of transcription (Emerman & Temin, Cell, 39:449-67 (1984)). This strategy can also be used to eliminate downstream transcription from the 3' LTR into genomic DNA (Herman & Coffin, Science, 236:845-48 (1987)). This is of particular concern in human gene therapy where it is of critical importance to prevent the adventitious activation of an endogenous oncogene.

The plasmid vector used to produce the viral genome within a host cell/packaging cell will also include transcriptional regulatory control sequences operably linked to the lentiviral genome to direct transcription of the genome in a host cell/packaging cell. These regulatory sequences may be the natural sequences associated with the transcribed lentiviral sequence, i.e. the 5' U3 region, or they may be a heterologous promoter such as another viral promoter, for example the CMV promoter. Some lentiviral genomes require additional sequences for efficient virus production. For example, in the case of HIV, the rev and RRE sequences are preferably included; however the requirement for rev and RRE may be reduced or eliminated by codon optimization (See U.S. Patent Application Publication No. 2010/0273996, incorporated by reference). Alternative sequences which perform the same function, as the rev/RRE system are also known. For example, a functional analogue of the rev/RRE system is found in the Mason Pfizer monkey virus. This is known as the constitutive transport element (CTE) and comprises an RRE-type sequence in the genome which is believed to interact with a factor in the infected cell. The cellular factor can be thought of as a rev analogue. Thus, CTE may be used as an alternative to the rev/RRE system. Any other functional equivalents which are known or become available may be relevant to the invention. For example, the Rex protein of HTLV-I can functionally replace the Rev protein of HIV-1. It is also known that Rev and Rex have similar effects to IRE-BP.

In a particular embodiment, the lentiviral vector according to the present invention consists of a self-inactivating minimal lentiviral vector, derived from Equine Infectious Anemia Virus (EIAV), encoding a shRNA directed against Nurr1. The vector may be produced by the transient transfection of cells (e.g. HEK293T cells) with three plasmids, encoding for: (1) the recombinant EIAV ProSavin® (Oxford BioMedica pic, Oxford UK) vector genome (Farley et al., J. Gen. Med., 9:345-56 (2007); U.S. Pat. No. 7,259,015, incorporated by reference); (2) the synthetic EIAV gag/pol expression vector (pESGPK, U.S. Patent Application Publication No's 2013/0281975 and 2010/0273996, incorporated by reference) and (3) the VSV-G envelope expression vector (pHGK).

3. Herpes Simplex Virus

Herpes simplex virus (HSV) vectors may also be utilized to express interfering nucleic acids in the nervous system. The genome of the type-1 (HSV-1) is about 150 kb of linear, double-stranded DNA, featuring about 70 genes. Many viral genes may be deleted without the virus losing its ability to propagate. The "immediately early" (IE) genes are transcribed first. They encode trans-acting factors which regulate expression of other viral genes. The "early" (E) gene products participate in replication of viral DNA. The late genes encode the structural components of the virion as well as proteins which turns on transcription of the IE and E genes or disrupt host cell protein translation.

The HSV vector may be a plasmid-based system, whereby a plasmid vector (termed an amplicon) is generated that contains a nucleotide sequence encoding the interfering nucleic acid and two cis-acting HSV recognition signals. The recognition signals are the origin of DNA replication and the cleavage packaging signal, which encode no HSV gene products. Thus, helper virus is required to replicate the amplicon and package it into an HSV coat. The vector therefore expresses no viral gene products within the recipient cell, and recombination with or reactivation of latent viruses by the vector is limited due to the minimal amount of HSV DNA sequence present within the defective HSV vector genome.

Examples of HSV-mediated gene therapy are well known in the art (Breakefield & DeLuca, New Biologist, 3:203-18 (1991); Ho & Mocarski, Virology, 167:279-93 (1988); Palella, et al., Molecular & Cellular Biology, 8:457-60 (1988); Pallela et al., Gene, 80:137-44 (1988); Andersen et al., Human Gene Therapy, 3:487-99 (1992); Kaplitt et al., Current Topics Neuroendocrinology, 11:169-91 (1993); Spaele & Frenkel, Cell, 30:295-04 (1982); Kaptitt et al., Molecular & Cellular Neuroscience, 2:320-30 (1991); Federoff et al., Proceedings Nat. Acad. Sci. USA, 89:1636-40 (1992)).

4. Adenovirus

Adenovirus vectors may be utilized to express interfering nucleic acids in the nervous system. The adenovirus genome consists of about 36 kb of double-stranded DNA. Adenoviruses target airway epithelial cells, but are also capable of infecting neurons. Recombinant adenovirus vectors have been used as gene transfer vehicles for non-dividing cells. These vectors are similar to recombinant HSV vectors, since the adenovirus E1a immediate-early gene is removed but most viral genes are retained. Since the E1a gene is small (roughly 1.5 kb) and the adenovirus genome is approximately one-third of the size of the HSV genome, other non-essential adenovirus genes are removed in order to insert a foreign gene within the adenovirus genome.

Examples of adenovirus-mediated gene therapy are well known in the art (Akli et al., Nature Genetics, 3:224-28 (1993); La Salle et al., Science, 259:988-90 (1993), La Salle, Nature Genetics, 3:1-2 (1993); Neve, Trends Biochemical Sci., 16:251-53 (1993)).

C. Non-Viral Vectors

The interfering nucleic acid or a nucleic acid encoding the interfering nucleic acid can be delivered using a non-viral delivery system. This includes delivery of a nucleic acid to the desired tissues in colloidal dispersion systems that include, for example, macromolecule complexes, nanocapsules, microspheres, beads, and lipid-based systems including oil-in-water emulsions, micelles, mixed micelles, and liposomes.

Liposomes are artificial membrane vesicles which are useful as delivery vehicles in vitro and in vivo. In order for a liposome to be an efficient gene transfer vehicle, the following characteristics should be present: (1) encapsulation of the genetic material at high efficiency while not compromising the biological activity; (2) preferential and substantial binding to a target cell in comparison to nontarget cells; (3) delivery of the aqueous contents of the vesicle to the target cell cytoplasm at high efficiency; and (4) accurate and effective expression of genetic information (Mannino et al., BioTechniques, 6:682-90 (1988)).

Liposomes suitable for use in the methods described herein can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. Examples of suitable lipids liposomes production include phosphatidyl compounds, such as phosphatidylglycerol, phosphatidylcholine, phosphatidylserine, phosphatidylethanolamine, sphingolipids, cerebrosides, and gangliosides. Additional examples of lipids include, but are not limited to, polylysine, protamine, sulfate and 3β-[N—(N',N'-dimethylaminoethane) carbamoyl] cholesterol. A variety of methods are known for preparing liposomes, for example, as described in Szoka et al., Annual Rev. Biophysics & Bioengineering, 9:467-08 (1980); and U.S. Pat. Nos. 4,235,871; 4,501,728; 4,837,028; and 5,019,369, which are herein incorporated by reference.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 angstroms, containing an aqueous solution in the core.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure.

Opsonization-inhibiting moieties for use in preparing the liposomes described herein are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, herein incorporated by reference.

In some embodiments, opsonization inhibiting moieties suitable for modifying liposomes are water-soluble polymers with a number-average molecular weight from about 500 to about 40,000 daltons, or from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. In some embodiments, the opsonization-inhibiting moiety is a PEG, PPG, or derivatives thereof. Liposomes modified with PEG or PEG-derivatives are sometimes called "PEGylated liposomes."

D. Pharmaceutical Formulations

Formulations of pharmaceutically-acceptable excipients and carrier solutions are well-known to those of skill in the art, as is the development of suitable dosing and treatment regimens for using the particular compositions described herein in a variety of treatment regimens. Typically, these formulations may contain at least about 0.1% of the active ingredient or more, although the percentage of the active ingredient(s) may, of course, be varied and may conveniently be between about 1 or 2% and about 70% or 80% or more of the weight or volume of the total formulation. Naturally, the amount of active ingredient in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual subject.

Sterile injectable solutions are prepared by incorporating the virus, nucleic acid, or other vector in the required amount in the appropriate solvent with various of the other ingredients enumerated herein and known to those skilled in the art, as required, followed by filtered sterilization. Generally, dispersions are prepared by incorporating the various sterilized active ingredients into a sterile vehicle which contains the basic dispersion medium and the required other ingredients from those enumerated herein. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may also be formulated in a neutral or salt form. Pharmaceutically-acceptable salts, include the acid addition salts (formed with the free amino groups of the AAV capsid) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

Carriers include any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions.

Delivery vehicles such as liposomes, nanocapsules, microparticles, microspheres, lipid particles, vesicles, and the like, may be used for the introduction of the compositions of the present invention into suitable host cells. In particular, interfering nucleic acids may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the AAV constructs disclosed herein. The formation and use of liposomes is generally known to those of skill in the art. Recently, liposomes were developed with improved serum stability and circulation half-times (U.S. Pat. No. 5,741,516, incorporated by reference). Further, various methods of liposome and liposome like preparations as potential drug carriers have been described (U.S. Pat. Nos. 5,567,434; 5,552,157; 5,565,213; 5,738,868 and 5,795,587, incorporated by reference).

Alternatively, nanocapsule formulations of the AAV vector may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

E. Administration of the Composition

In one embodiment of the invention, the viral and nucleic acid vectors will be formulated into pharmaceutical compositions and administered by injection directly into the striatum. If desired, an Omaya reservoir can be placed within the surgical site to enable repeat administration of a composition.

Precise delivery of a composition into the striatum can be conducted using stereotactic microinjection techniques. For example, the subject being treated can be placed within a MRI-compatible stereotactic frame base and then imaged using high resolution MRI to determine the three-dimensional positioning for the particular injection. The MRI images are then transferred to a computer having the appropriate stereotactic software, and a number of images are used to determine a target site and trajectory for a microinjection. The software translates the trajectory into three-dimensional coordinates that are appropriate for the stereotactic frame. In the case of intracranial delivery, the skull will be exposed, burr holes will be drilled above the entry site, and the stereotactic apparatus positioned with the needle implanted at a predetermined depth. A pharmaceutical composition comprising a viral or nucleic acid vector can then be microinjected at the selected target sites. In some embodiments, the composition is injected by an osmotic pump or an infusion pump, such as a convection-enhanced delivery device. The spread of the vector from the site of injection will be a function of diffusion, which may be controlled by adjusting the concentration of the vector in the pharmaceutical composition.

In some embodiments, the composition is injected during the implantation of a brain pacemaker for deep brain stimulation. In other embodiments, the composition is injected during a pallidotomy.

EXEMPLIFICATION

Example 1

Increasing the Expression of Nurr1 Increases the Severity of LIDs

Adult male Sprague-Dawley rats were rendered parkinsonian using 6-hydroxydopamine. Following the establishment of a stable lesion (4 weeks), animals received recombinant adeno-associated virus type 2/5 overexpressing either Nurr1 or GFP in the denervated striatum. Four weeks following the vector injection, the animals were subjected to escalating doses of L-DOPA (2 to 24 mg/kg) two-to-three times per week. The animals were evaluated for LIDs at the same time they received L-DOPA. No changes in LID severity were observed with low levels of L-DOPA administration or without L-DOPA priming. At doses exceeding 12 mg/kg, Nurr1 treated animals exhibited significantly elevated LID scores, which persisted over a longer period of time than the AAV-GFP injected control.

Example 2

Decreasing the Expression of Nurr1 Decreases the Severity of LIDs in Rat Model

Preparation of the vector: The Nurr1 protein is knocked-down via the use of short hairpin RNA (shRNA). A nucleotide sequence encoding a shRNA is cloned and inserted into an AAV plasmid backbone (AAV-shRNA), and a scrambled shRNA is cloned and inserted a different AAV plasmid backbone as a control (AAV-control). Both plasmids contain a nucleotide sequence encoding the gene for green fluorescent protein (GFP) as a reporter. The expression of the transgene is driven by the chicken beta actin/cytomegalovirus enhancer (CβA/CMV). Vectors containing AAV2 ITRs are packaged into AAV5 capsids via co-transfection with a plasmid containing the AAV rep and cap genes and adenovirus helper functions. Particles are purified using iodixanol gradients and Q-sepharose chromatography, and dotblot is used to determine vector titers. Viral preparations are stored at 4° C. and kept on wet ice during surgical procedures. All pipette, syringe, and centrifuge tube surfaces are coated with SigmaCote (Sigma-Aldrich, St. Louis, Mo.) prior to coming in contact with virus to minimize the binding of viral particles.

LIDs model: Adult male Sprague-Dawley rats are rendered parkinsonian using 6-hydroxydopamine. Following the establishment of a stable lesion (4 weeks), the animals are subjected to escalating doses of L-DOPA (2 to 24 mg/kg) two-to-three times per week. The animals are evaluated for LIDs at the same time they receive L-DOPA.

Delivery of vector to the striatum: Sprague Dawley rats are unilaterally injected in the striatum with $10^{12}$ to $10^{14}$ recombinant viral particles. First, rats are anesthetized with 5% isoflurane in oxygen for induction and 2% isoflurane in oxygen for maintenance. Rats are placed in a stereotaxic frame and two 2 µl injections of either AAV-shRNA or AAV-control are injected into the striatum using a Hamilton syringe fitted with a glass capillary needle (Hamilton Gas Tight syringe 80,000, 26 s/2" needle; Hamilton, Reno, Nev.; coated with SigmaCote). The vector injection begins immediately after the needle is lowered to the site. Vector is injected at a rate of 0.5 µl/minute, and the needle remains in place after the injection for an additional five minutes before retraction.

Example 3

Decreasing the Expression of Nurr1 Decreases the Severity of LIDs in Monkey Model LIDs model: Rhesus monkeys are excellent models for studying LIDs based on the evolution of their parkinsonian symptoms. Animals are lesioned by infusing 2.5-3.5 mg of 1-methyl-4-phenyl-1,2,3,6-tetrahydropyridine HCL (MPTP-HCL) through the right internal carotid artery (referred to as ipsilateral side) followed by 4 I.V. doses of 0.3 mg/kg of MPTP-HCL (referred to as contralateral side) until a stable, overlesioned hemi-parkinsonian syndrome is achieved (Eberling, Brain Research, 805:259-62 (1998)). The primate MPTP model is the gold standard model of evaluation prior to human trials (Langston, Trends Pharmacological Sci., 6:375-78 (1985)). MPTP is converted in the CNS to 1-methyl-4-phenylpyridinium (MPP+) by monoamine oxidase B. MPP+ is a potent neurotoxin which causes degeneration of the nigral dopaminergic neurons and loss of the nigro-striatal dopamine pathway, as seen in Parkinson's disease. Following the establishment of a stable lesion, the animals are subjected to escalating doses of L-DOPA and evaluated for LIDs.

Delivery of vector to the striatum: In the surgery room, a sterile field is created to prepare the infusion system. Infusion cannulae are flushed with saline to assess the integrity between the needle and tubing interface. Sterile infusion cannulae and loading lines are connected using the appropriate fittings with extreme caution taken to prevent the collection of air bubbles in the system. Non-sterile oil infusion lines are prepared and 1 ml gas tight Hamilton syringes filled with oil are attached to an infusion pump. Six infusion cannulae are fitted onto microdialysis holders (3 cannulae per holder) and mounted onto a stereotactic tower. Following the union of the oil and loading lines, the needle cannulae are primed with AAV and the infusion system is transferred to the surgery table. Initial infusion rates are set at 0.1 pl/minute, the lines are visually inspected to ensure a smooth flow of fluid through the system, and the cannulae are manually lowered to their target sites. A final visual inspection is performed to check for any air bubbles in the infusion system.

The cannula system consists of three components: (i) a sterile infusion cannula; (ii) a sterile loading line housing AAV-shRNA or AAV-control; and (iii) a non-sterile infusion line containing oil. The infusion cannula consists of 27 G needles (outer diameter, 0.03"; inner diameter, 0.06") fitted with fused silica (outer diameter, 0.016", inner diameter, 0.008"), and placed in Teflon tubing (0.03" ID) such that the distal tip of the silica extends approximately 15 mm out of the tubing. The needle is secured into the tubing using superglue and the system is checked for leaks prior to use. At the proximal end of the tubing, a Tefzel fitting and ferrule are attached to connect the adjacent loading line.

Loading and infusion lines consist of 50 cm sections of Teflon tubing (outer diameter, 0.062"; inner diameter, 0.03") fitted with Tefzel 1/16" ferrules, unions, and male Luer-lock adapters at the distal ends. The sterile loading lines accommodate up to a 1000 ml volume, and they are primed with saline prior to use.

The animals are initially sedated with Ketamine (10 mg/kg, i.m.), intubated, and prepped for surgery. A venous line is established using a 22 gauge catheter positioned in the cephalic or saphenous vein to deliver isotonic fluids at 5-10 ml/kg/hr. Isoflurane is delivered at 1-3% until the animal maintained a stable plane of anesthesia. The head is placed in an MRI compatible stereotactic frame according to pre-set values attained during a baseline MRI scan. The animal is instrumented with subcutaneous electrocardiogram electrodes and a rectal probe, and the body is covered with circulating water blankets to maintain a core temperature of 36-38° C. Electrocardiogram, heart rate, and body temperature are continuously monitored during the procedure. The head is prepped with Betadine and 70% ethanol, a sterile field is created, and a midline incision is performed through the skin, muscle, and fascia using electrocautery.

Gentle retraction of fascia and muscle allows for cranial exposure over cortical entry sites. A unilateral craniotomy is performed using a drill to expose a 3 cm×2 cm area of dura mater above the target sites. Multiple needle cannulae attached to a holder are stereotactically guided to striatal target sites. Surgical parameters for the unilateral infusion of AAV into the hemisphere ipsilateral to ICA MPTP infusion are summarized in Table I.

TABLE I

| Infusion parameters | |
|---|---|
| Infusion Volume | 30 µl per site |
| Infusion Rates | 0.1 µl/min (60 min) |
|  | 0.2 µl/min (60 min) |
|  | 0.4 µl/min (30 min) |
| Virus | AAV-shRNA; 1 × $10^{12}$ particles/ml |
| Control | AAV-control; 1 × $10^{12}$ particles/ml |

Approximately fifteen minutes following infusion, the cannulae assembly is raised at a rate of 1 mm/minute until it is out of the cortex. The cortex is rinsed with saline, the bone margins are trimmed with ronguers, and the wound site is closed in anatomical layers. Analgesics (Numorphan, 1M) and antibiotics (Flocillin, 1M) are administered as part of the surgical protocol. Animals are monitored for full recovery from anesthesia, placed in their home cages, and clinically observed for several days following surgery.

Example 4

Decreasing Nurr1 Activity in Human Subjects

Human Parkinson's patients suffering from LIDs are bilaterally infused with a total dose of $10^{10}$ to $10^{15}$ AAV-shRNA particles per subject in 100-1000 μL total volume. AAV-shRNA is administered to the striatum by intrastriatal infusion delivered by means of a stereotactically positioned cannula. The administration device includes a surgical stainless steel cannula with a stepped design to facilitate convection enhanced delivery, biocompatible Teflon tubing, and a syringe. The device is attached to a syringe pump to achieve a consistent rate of infusion of 1 μL per minute.

Post-surgical visits occur at 1, 2 and 4 weeks post-surgery. The visits at weeks 1 and 2 primarily involve post-surgical care, e.g. dressing change. Subjects are followed for a total of 6 months, with examinations occurring at 1-month intervals until the third month. Behavioral assessments will occur at baseline, three and six months.

INCORPORATION BY REFERENCE

All of the publications including patents, published patent applications, and non-patent literature cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method for treating dyskinesia in a subject in need thereof, comprising administering to the subject a therapeutically effective amount of a composition, wherein said composition comprises a nucleic acid molecule that encodes an antisense molecule, a small interfering RNA molecule (siRNA), a short hairpin RNA molecule (shRNA), or a microRNA molecule (miRNA) that targets a nuclear receptor related 1 protein ("Nurr1") and reduces the activity of said Nurr1 to thereby treat dyskinesia.

2. The method of claim 1, wherein said shRNA targets Nurr1 mRNA for degradation.

3. The method of claim 1, wherein the composition comprises a virus.

4. The method of claim 3, wherein the virus is an adeno-associated virus ("AAV"), adenovirus, herpes simplex virus, or lentivirus.

5. The method of claim 4, wherein the virus is AAV.

6. The method of claim 5, wherein the virus is AAV1.

7. The method of claim 3, wherein a genome of said virus comprises said nucleic acid molecule.

8. The method of claim 1, wherein administering comprises inserting the composition at a desired location.

9. The method of claim 8, wherein the desired location is the brain.

10. The method of claim 9, wherein the desired location is the striatum.

11. The method of claim 10, wherein the desired location is the denervated striatum.

12. The method of claim 8, wherein inserting comprises injecting the composition.

13. The method of claim 1, wherein the subject is a mammal.

14. The method of claim 1, wherein the subject is a primate, porcine, canine, ovine, or rodent.

15. The method of 1, wherein the subject is a human.

16. A method for treating levodopa-induced dyskinesia in a subject in need thereof, comprising administering to the subject a therapeutically effective amount of a composition, wherein:
the composition comprises a nucleic acid molecule that encodes an antisense molecule, a small interfering RNA molecule (siRNA), a short hairpin RNA molecule (shRNA), or a microRNA molecule (miRNA) that targets a nuclear receptor related 1 protein ("Nunn1");
administering comprises inserting the composition into the brain; and
the composition reduces the activity of said Nurr1 to thereby treat levodopa-induced dyskinesia.

* * * * *